United States Patent
Young et al.

(10) Patent No.: US 9,445,751 B2
(45) Date of Patent: Sep. 20, 2016

(54) DEVICE AND METHOD OF MONITORING A POSITION AND PREDICTING AN EXIT OF A SUBJECT ON OR FROM A SUBSTRATE

(71) Applicant: SleepIQ Labs, Inc., San Jose, CA (US)

(72) Inventors: Steven J. Young, Los Gatos, CA (US); Carl Hewitt, San Jose, CA (US); Al Luckow, Ben Lomond, CA (US)

(73) Assignee: SleepIQ Labs, Inc., San Jose, CA (US)

( * ) Notice: Subject to any disclaimer, the term of this patent is extended or adjusted under 35 U.S.C. 154(b) by 79 days.

(21) Appl. No.: 13/945,554

(22) Filed: Jul. 18, 2013

(65) Prior Publication Data

US 2015/0025327 A1 Jan. 22, 2015

(51) Int. Cl.
*A61B 5/11* (2006.01)
*A61B 5/00* (2006.01)
*A61B 5/0205* (2006.01)
*A61B 5/024* (2006.01)
*A61B 5/08* (2006.01)

(52) U.S. Cl.
CPC ............ *A61B 5/1115* (2013.01); *A61B 5/6892* (2013.01); *A61B 5/0022* (2013.01); *A61B 5/024* (2013.01); *A61B 5/0205* (2013.01); *A61B 5/0816* (2013.01); *A61B 5/1116* (2013.01); *A61B 5/6891* (2013.01); *A61B 5/6894* (2013.01); *A61B 5/7275* (2013.01); *A61B 2562/0247* (2013.01)

(58) Field of Classification Search
CPC .. A61B 5/0022; A61B 5/024; A61B 5/0205; A61B 5/0816; A61B 5/1115; A61B 5/1116; A61B 5/6891; A61B 5/6892; A61B 5/6894; A61B 5/7275; A61B 2562/0247

USPC .......................... 600/300, 301, 509, 529, 587
See application file for complete search history.

(56) References Cited

U.S. PATENT DOCUMENTS

| | | | |
|---|---|---|---|
| 3,727,606 | A | 4/1973 | Sielaff |
| 4,146,885 | A | 3/1979 | Lawson, Jr. |
| 4,299,233 | A | 11/1981 | Lemelson |

(Continued)

FOREIGN PATENT DOCUMENTS

EP 2 250 988 11/2010

OTHER PUBLICATIONS

Notification of Transmittal, the International Search Report and the Written Opinion of the International Searching Authority dated Nov. 24, 2014 from the corresponding International Application No. PCT/US2014/047157.

(Continued)

*Primary Examiner* — Gary Jackson
*Assistant Examiner* — Boniface N Nganga
(74) *Attorney, Agent, or Firm* — Fish & Richardson P.C.

(57) ABSTRACT

Methods and devices for monitoring the position of a subject are disclosed. One such method includes sensing pressure waves generated by the subject moving on a divided bladder comprising interleaved portions, generating signals indicative of the pressure waves for each of the interleaved portions, and sending the signals to a processor. The method further includes determining the position of the subject based on the difference between the signals from each of the interleaved portions and generating a pattern for the subject. The pattern includes the presence and/or position of the subject over time. The method further includes predicting an action such as an exit of the subject from the divided bladder based on comparing a current pattern for the subject to previous patterns for the subject.

24 Claims, 8 Drawing Sheets

(56) References Cited

U.S. PATENT DOCUMENTS

| | | | |
|---|---|---|---|
| 4,438,771 A | 3/1984 | Friesen et al. | |
| 4,657,026 A | 4/1987 | Tagg | |
| 4,662,012 A | 5/1987 | Tarbet | |
| 4,766,628 A | 8/1988 | Walker | |
| 4,788,729 A | 12/1988 | Walker | |
| 4,829,616 A | 5/1989 | Walker | |
| 4,890,344 A | 1/1990 | Walker | |
| 4,897,890 A | 2/1990 | Walker | |
| 4,908,895 A | 3/1990 | Walker | |
| 4,991,244 A | 2/1991 | Walker | |
| 5,062,169 A | 11/1991 | Kennedy et al. | |
| 5,140,309 A * | 8/1992 | Gusakov | 340/573.4 |
| 5,144,706 A | 9/1992 | Walker et al. | |
| 5,170,522 A | 12/1992 | Walker | |
| 5,197,490 A | 3/1993 | Steiner et al. | |
| 5,459,452 A | 10/1995 | DePonte | |
| 5,509,154 A | 4/1996 | Shafer et al. | |
| 5,515,865 A | 5/1996 | Scanlon | |
| 5,564,140 A | 10/1996 | Shoenhair et al. | |
| 5,642,546 A | 7/1997 | Shoenhair | |
| 5,652,484 A | 7/1997 | Shafer et al. | |
| 5,675,855 A | 10/1997 | Culp | |
| 5,684,460 A | 11/1997 | Scanlon | |
| 5,699,038 A | 12/1997 | Ulrich et al. | |
| 5,724,990 A | 3/1998 | Ogino | |
| 5,765,246 A | 6/1998 | Shoenhair | |
| 5,771,511 A | 6/1998 | Kummer et al. | |
| 5,796,340 A | 8/1998 | Miller | |
| 5,844,488 A | 12/1998 | Musick | |
| 5,848,450 A | 12/1998 | Oexman et al. | |
| 5,903,941 A | 5/1999 | Shafer et al. | |
| 5,904,172 A | 5/1999 | Gifft et al. | |
| 5,948,303 A | 9/1999 | Larson | |
| 5,964,720 A | 10/1999 | Pelz | |
| 5,989,193 A | 11/1999 | Sullivan | |
| 6,024,699 A | 2/2000 | Surwit et al. | |
| 6,037,723 A | 3/2000 | Shafer et al. | |
| 6,058,537 A | 5/2000 | Larson | |
| 6,062,216 A | 5/2000 | Corn | |
| 6,108,844 A | 8/2000 | Kraft et al. | |
| 6,120,441 A | 9/2000 | Griebel | |
| 6,146,332 A | 11/2000 | Pinsonneault et al. | |
| 6,147,592 A | 11/2000 | Ulrich et al. | |
| 6,161,231 A | 12/2000 | Kraft et al. | |
| 6,202,239 B1 | 3/2001 | Ward et al. | |
| 6,208,250 B1 | 3/2001 | Dixon et al. | |
| 6,234,642 B1 | 5/2001 | Bokaemper | |
| 6,272,378 B1 | 8/2001 | Baumgart-Schmitt | |
| 6,386,201 B1 | 5/2002 | Fard | |
| 6,396,224 B1 | 5/2002 | Luff et al. | |
| 6,397,419 B1 | 6/2002 | Mechache | |
| 6,438,776 B2 | 8/2002 | Ferrand et al. | |
| 6,445,287 B1 * | 9/2002 | Schofield et al. | 340/442 |
| 6,450,957 B1 | 9/2002 | Yoshimi et al. | |
| 6,468,234 B1 | 10/2002 | Ford et al. | |
| 6,483,264 B1 | 11/2002 | Shafer et al. | |
| 6,485,441 B2 | 11/2002 | Woodward | |
| 6,546,580 B2 | 4/2003 | Shimada | |
| 6,547,743 B2 | 4/2003 | Brydon | |
| 6,561,047 B1 | 5/2003 | Gladney | |
| 6,566,833 B2 | 5/2003 | Bartlett | |
| 6,578,871 B2 * | 6/2003 | Gray et al. | 280/735 |
| 6,686,711 B2 | 2/2004 | Rose et al. | |
| 6,708,357 B2 | 3/2004 | Gaboury et al. | |
| 6,719,708 B1 | 4/2004 | Jansen | |
| 6,763,541 B2 | 7/2004 | Mahoney et al. | |
| 6,778,090 B2 | 8/2004 | Newham | |
| 6,804,848 B1 | 10/2004 | Rose | |
| 6,832,397 B2 | 12/2004 | Gaboury et al. | |
| 6,840,117 B2 | 1/2005 | Hubbard, Jr. | |
| 6,840,907 B1 | 1/2005 | Brydon | |
| 6,847,301 B1 | 1/2005 | Olson | |
| 6,878,121 B2 | 4/2005 | Krausman | |
| 6,883,191 B2 | 4/2005 | Gaboury et al. | |
| 6,993,380 B1 | 1/2006 | Modarres | |
| 7,030,764 B2 | 4/2006 | Smith et al. | |
| 7,041,049 B1 | 5/2006 | Raniere | |
| 7,077,810 B2 | 7/2006 | Lange et al. | |
| 7,150,718 B2 | 12/2006 | Okada | |
| 7,237,287 B2 | 7/2007 | Weismiller et al. | |
| 7,253,366 B2 * | 8/2007 | Bhai | 177/45 |
| 7,304,580 B2 | 12/2007 | Sullivan et al. | |
| 7,314,451 B2 | 1/2008 | Halperin et al. | |
| 7,321,811 B1 | 1/2008 | Rawls-Meehan | |
| 7,330,127 B2 | 2/2008 | Price et al. | |
| 7,389,554 B1 | 6/2008 | Rose | |
| 7,396,331 B2 | 7/2008 | Mack | |
| 7,429,247 B2 | 9/2008 | Okada et al. | |
| 7,437,787 B2 | 10/2008 | Bhai | |
| 7,465,280 B2 | 12/2008 | Rawls-Meehan | |
| 7,480,951 B2 | 1/2009 | Weismiller | |
| 7,506,390 B2 | 3/2009 | Dixon et al. | |
| 7,520,006 B2 | 4/2009 | Menkedick et al. | |
| 7,524,279 B2 | 4/2009 | Auphan | |
| 7,532,934 B2 | 5/2009 | Lee et al. | |
| 7,538,659 B2 | 5/2009 | Ulrich | |
| 7,568,246 B2 | 8/2009 | Weismiller et al. | |
| 7,637,859 B2 | 12/2009 | Lindback et al. | |
| 7,652,581 B2 | 1/2010 | Gentry et al. | |
| 7,666,151 B2 | 2/2010 | Sullivan et al. | |
| 7,669,263 B2 | 3/2010 | Menkedick et al. | |
| 7,676,872 B2 | 3/2010 | Block et al. | |
| 7,685,663 B2 | 3/2010 | Rawls-Meehan | |
| 7,699,784 B2 | 4/2010 | Wan et al. | |
| 7,717,848 B2 | 5/2010 | Heruth et al. | |
| 7,749,154 B2 | 7/2010 | Cornel | |
| 7,784,128 B2 | 8/2010 | Kramer | |
| 7,785,257 B2 | 8/2010 | Mack et al. | |
| 7,805,785 B2 | 10/2010 | Rawls-Meehan | |
| 7,841,031 B2 | 11/2010 | Rawls-Meehan | |
| 7,849,545 B2 | 12/2010 | Flocard et al. | |
| 7,854,031 B2 | 12/2010 | Rawls-Meehan | |
| 7,860,723 B2 | 12/2010 | Rawls-Meehan | |
| 7,862,523 B2 | 1/2011 | Ruotoistenmaki | |
| 7,865,988 B2 | 1/2011 | Koughan et al. | |
| 7,868,757 B2 | 1/2011 | Radivojevic et al. | |
| 7,869,903 B2 | 1/2011 | Turner et al. | |
| 7,930,783 B2 | 4/2011 | Rawls-Meehan | |
| 7,933,669 B2 | 4/2011 | Rawls-Meehan | |
| 7,953,613 B2 | 5/2011 | Gizewski | |
| 7,954,189 B2 | 6/2011 | Rawls-Meehan | |
| 7,956,755 B2 | 6/2011 | Lee et al. | |
| 7,967,739 B2 | 6/2011 | Auphan | |
| 7,971,300 B2 | 7/2011 | Wilker, Jr. | |
| 7,979,169 B2 | 7/2011 | Rawls-Meehan | |
| 8,019,486 B2 | 9/2011 | Rawls-Meehan | |
| 8,020,230 B2 | 9/2011 | Rawls-Meehan | |
| 8,028,363 B2 | 10/2011 | Rawls-Meehan | |
| 8,032,263 B2 | 10/2011 | Rawls-Meehan | |
| 8,032,960 B2 | 10/2011 | Rawls-Meehan | |
| 8,046,114 B2 | 10/2011 | Rawls-Meehan | |
| 8,046,115 B2 | 10/2011 | Rawls-Meehan | |
| 8,046,116 B2 | 10/2011 | Rawls-Meehan | |
| 8,046,117 B2 | 10/2011 | Rawls-Meehan | |
| 8,050,805 B2 | 11/2011 | Rawls-Meehan | |
| 8,052,612 B2 | 11/2011 | Tang | |
| 8,065,764 B2 | 11/2011 | Kramer | |
| 8,069,852 B2 | 12/2011 | Burton | |
| 8,073,535 B2 | 12/2011 | Jung et al. | |
| 8,078,269 B2 | 12/2011 | Suzuki et al. | |
| 8,078,336 B2 | 12/2011 | Rawls-Meehan | |
| 8,078,337 B2 | 12/2011 | Rawls-Meehan | |
| 8,083,682 B2 | 12/2011 | Dalal et al. | |
| 8,090,478 B2 | 1/2012 | Skinner et al. | |
| 8,092,399 B2 | 1/2012 | Sasaki | |
| 8,094,013 B1 | 1/2012 | Lee et al. | |
| 8,096,960 B2 | 1/2012 | Loree et al. | |
| 8,146,191 B2 | 4/2012 | Bobey et al. | |
| 8,150,562 B2 | 4/2012 | Rawls-Meehan | |
| 8,166,589 B2 | 5/2012 | Hijlkema | |
| 8,181,296 B2 | 5/2012 | Rawls-Meehan | |
| 8,266,742 B2 | 9/2012 | Andrienko | |
| 8,272,892 B2 | 9/2012 | McNeely et al. | |
| 8,276,585 B2 | 10/2012 | Buckley | |

(56) References Cited

U.S. PATENT DOCUMENTS

| | | |
|---|---|---|
| 8,279,057 B2 | 10/2012 | Hirose |
| 8,280,748 B2 | 10/2012 | Allen |
| 8,281,433 B2 | 10/2012 | Riley et al. |
| 8,282,452 B2 | 10/2012 | Grigsby et al. |
| 8,284,047 B2 | 10/2012 | Collins, Jr. |
| 8,287,452 B2 | 10/2012 | Young et al. |
| 8,336,369 B2 | 12/2012 | Mahoney |
| 8,341,784 B2 | 1/2013 | Scott |
| 8,341,786 B2 | 1/2013 | Oexman et al. |
| 8,348,840 B2 | 1/2013 | Heit et al. |
| 8,350,709 B2 | 1/2013 | Receveur |
| 8,375,488 B2 | 2/2013 | Rawls-Meehan |
| 8,376,954 B2 | 2/2013 | Lange et al. |
| 8,382,484 B2 | 2/2013 | Wetmore et al. |
| 8,386,008 B2 | 2/2013 | Yuen et al. |
| 8,398,538 B2 | 3/2013 | Dothie |
| 8,403,865 B2 | 3/2013 | Halperin et al. |
| 8,413,274 B2 | 4/2013 | Weismiller et al. |
| 8,421,606 B2 | 4/2013 | Collins, Jr. et al. |
| 8,428,696 B2 | 4/2013 | Foo |
| 8,444,558 B2 | 5/2013 | Young et al. |
| 8,491,492 B2 | 7/2013 | Shinar et al. |
| 8,517,953 B2 | 8/2013 | Lange et al. |
| 8,620,615 B2 | 12/2013 | Oexman |
| 8,672,853 B2 | 3/2014 | Young |
| 8,679,034 B2 | 3/2014 | Halperin et al. |
| 8,682,457 B2 | 3/2014 | Rawls-Meehan |
| 8,769,747 B2 | 7/2014 | Mahoney et al. |
| 8,840,564 B2 | 9/2014 | Pinhas et al. |
| 8,931,329 B2 | 1/2015 | Mahoney et al. |
| 8,966,689 B2 | 3/2015 | McGuire et al. |
| 8,973,183 B1* | 3/2015 | Palashewski ............. 5/482 |
| 8,984,687 B2 | 3/2015 | Stusynski et al. |
| 2002/0124311 A1 | 9/2002 | Peftoulidis |
| 2003/0045806 A1 | 3/2003 | Brydon |
| 2003/0095263 A1* | 5/2003 | Varshneya et al. .......... 356/477 |
| 2003/0128125 A1 | 7/2003 | Burbank et al. |
| 2003/0166995 A1 | 9/2003 | Jansen |
| 2003/0182728 A1 | 10/2003 | Chapman et al. |
| 2003/0221261 A1 | 12/2003 | Tarbet et al. |
| 2004/0049132 A1 | 3/2004 | Barron et al. |
| 2004/0111045 A1* | 6/2004 | Sullivan et al. .............. 600/595 |
| 2005/0022606 A1 | 2/2005 | Partin et al. |
| 2005/0038326 A1 | 2/2005 | Mathur |
| 2005/0072250 A1* | 4/2005 | Brown .................... 73/862.581 |
| 2005/0091751 A1 | 5/2005 | Davis |
| 2005/0115561 A1 | 6/2005 | Stahmann et al. |
| 2005/0190068 A1 | 9/2005 | Gentry et al. |
| 2005/0283039 A1 | 12/2005 | Cornel |
| 2006/0020178 A1 | 1/2006 | Sotos et al. |
| 2006/0031996 A1 | 2/2006 | Rawls-Meehan |
| 2006/0047217 A1 | 3/2006 | Mirtalebi |
| 2006/0065060 A1 | 3/2006 | Ito et al. |
| 2006/0108168 A1* | 5/2006 | Fischer et al. .............. 180/273 |
| 2006/0129047 A1* | 6/2006 | Ruotoistenmaki ........... 600/483 |
| 2006/0152378 A1 | 7/2006 | Lokhorst |
| 2006/0162074 A1 | 7/2006 | Bader |
| 2007/0008156 A1* | 1/2007 | Ueda et al. .................. 340/575 |
| 2007/0118054 A1 | 5/2007 | Pinhas et al. |
| 2007/0149883 A1 | 6/2007 | Yesha |
| 2007/0179334 A1 | 8/2007 | Groves et al. |
| 2007/0180047 A1 | 8/2007 | Dong et al. |
| 2007/0180618 A1 | 8/2007 | Weismiller et al. |
| 2007/0276202 A1 | 11/2007 | Raisanen et al. |
| 2008/0052837 A1 | 3/2008 | Blumberg |
| 2008/0071200 A1 | 3/2008 | Rawls-Meehan |
| 2008/0077020 A1* | 3/2008 | Young et al. ................ 600/484 |
| 2008/0092291 A1 | 4/2008 | Rawls-Meehan |
| 2008/0092292 A1 | 4/2008 | Rawls-Meehan |
| 2008/0092293 A1 | 4/2008 | Rawls-Meehan |
| 2008/0092294 A1 | 4/2008 | Rawls-Meehan |
| 2008/0093784 A1 | 4/2008 | Rawls-Meehan |
| 2008/0097774 A1 | 4/2008 | Rawls-Meehan |
| 2008/0097778 A1 | 4/2008 | Rawls-Meehan |
| 2008/0097779 A1 | 4/2008 | Rawls-Meehan |
| 2008/0104750 A1 | 5/2008 | Rawls-Meehan |
| 2008/0104754 A1 | 5/2008 | Rawls-Meehan |
| 2008/0104755 A1 | 5/2008 | Rawls-Meehan |
| 2008/0104756 A1 | 5/2008 | Rawls-Meehan |
| 2008/0104757 A1 | 5/2008 | Rawls-Meehan |
| 2008/0104758 A1 | 5/2008 | Rawls-Meehan |
| 2008/0104759 A1 | 5/2008 | Rawls-Meehan |
| 2008/0104760 A1 | 5/2008 | Rawls-Meehan |
| 2008/0104761 A1 | 5/2008 | Rawls-Meehan |
| 2008/0109959 A1 | 5/2008 | Rawls-Meehan |
| 2008/0109964 A1 | 5/2008 | Flocard et al. |
| 2008/0109965 A1 | 5/2008 | Mossbeck |
| 2008/0115272 A1 | 5/2008 | Rawls-Meehan |
| 2008/0115273 A1 | 5/2008 | Rawls-Meehan |
| 2008/0115274 A1 | 5/2008 | Rawls-Meehan |
| 2008/0115275 A1 | 5/2008 | Rawls-Meehan |
| 2008/0115276 A1 | 5/2008 | Rawls-Meehan |
| 2008/0115277 A1 | 5/2008 | Rawls-Meehan |
| 2008/0115278 A1 | 5/2008 | Rawls-Meehan |
| 2008/0115279 A1 | 5/2008 | Rawls-Meehan |
| 2008/0115280 A1 | 5/2008 | Rawls-Meehan |
| 2008/0115281 A1 | 5/2008 | Rawls-Meehan |
| 2008/0115282 A1 | 5/2008 | Rawls-Meehan |
| 2008/0120775 A1 | 5/2008 | Rawls-Meehan |
| 2008/0120776 A1 | 5/2008 | Rawls-Meehan |
| 2008/0120777 A1 | 5/2008 | Rawls-Meehan |
| 2008/0120778 A1 | 5/2008 | Rawls-Meehan |
| 2008/0120779 A1 | 5/2008 | Rawls-Meehan |
| 2008/0120784 A1 | 5/2008 | Warner et al. |
| 2008/0122616 A1 | 5/2008 | Warner |
| 2008/0126122 A1 | 5/2008 | Warner et al. |
| 2008/0126132 A1 | 5/2008 | Warner |
| 2008/0127418 A1 | 6/2008 | Rawls-Meehan |
| 2008/0127424 A1 | 6/2008 | Rawls-Meehan |
| 2008/0132808 A1* | 6/2008 | Lokhorst et al. ............ 600/595 |
| 2008/0147442 A1 | 6/2008 | Warner |
| 2008/0162171 A1 | 7/2008 | Rawls-Meehan |
| 2008/0169931 A1* | 7/2008 | Gentry et al. ............. 340/573.1 |
| 2008/0189865 A1* | 8/2008 | Bhai ................................ 5/706 |
| 2008/0216248 A1* | 9/2008 | Phillips .............. A61G 7/05769 5/713 |
| 2008/0275314 A1 | 11/2008 | Mack et al. |
| 2008/0281611 A1 | 11/2008 | Rawls-Meehan |
| 2008/0281612 A1 | 11/2008 | Rawls-Meehan |
| 2008/0281613 A1 | 11/2008 | Rawls-Meehan |
| 2008/0288272 A1 | 11/2008 | Rawls-Meehan |
| 2008/0288273 A1 | 11/2008 | Rawls-Meehan |
| 2008/0306351 A1 | 12/2008 | Izumi |
| 2008/0307582 A1 | 12/2008 | Flocard et al. |
| 2009/0018853 A1 | 1/2009 | Rawls-Meehan |
| 2009/0018854 A1 | 1/2009 | Rawls-Meehan |
| 2009/0018855 A1 | 1/2009 | Rawls-Meehan |
| 2009/0018856 A1 | 1/2009 | Rawls-Meehan |
| 2009/0018857 A1 | 1/2009 | Rawls-Meehan |
| 2009/0018858 A1 | 1/2009 | Rawls-Meehan |
| 2009/0024406 A1 | 1/2009 | Rawls-Meehan |
| 2009/0037205 A1 | 2/2009 | Rawls-Meehan |
| 2009/0043595 A1 | 2/2009 | Rawls-Meehan |
| 2009/0064420 A1 | 3/2009 | Rawls-Meehan |
| 2009/0100599 A1 | 4/2009 | Rawls-Meehan |
| 2009/0121660 A1 | 5/2009 | Rawls-Meehan |
| 2009/0139029 A1 | 6/2009 | Rawls-Meehan |
| 2009/0183312 A1* | 7/2009 | Price et al. ...................... 5/706 |
| 2009/0192364 A1* | 7/2009 | Voto et al. ...................... 600/301 |
| 2009/0203972 A1 | 8/2009 | Heneghan et al. |
| 2009/0260158 A1* | 10/2009 | Kazuno et al. .................... 5/600 |
| 2009/0275808 A1 | 11/2009 | DiMaio et al. |
| 2009/0314354 A1 | 12/2009 | Chaffee |
| 2010/0025900 A1 | 2/2010 | Rawls-Meehan |
| 2010/0045474 A1* | 2/2010 | Hayes et al. .................. 340/666 |
| 2010/0090383 A1 | 4/2010 | Rawls-Meehan |
| 2010/0094139 A1 | 4/2010 | Brauers et al. |
| 2010/0099954 A1 | 4/2010 | Dickinson et al. |
| 2010/0152546 A1 | 6/2010 | Behan et al. |
| 2010/0170043 A1* | 7/2010 | Young et al. ...................... 5/706 |
| 2010/0174198 A1 | 7/2010 | Young et al. |
| 2010/0174199 A1* | 7/2010 | Young et al. .................. 600/484 |
| 2010/0191136 A1 | 7/2010 | Wolford |
| 2010/0199432 A1 | 8/2010 | Rawls-Meehan |

(56) References Cited

U.S. PATENT DOCUMENTS

| | | |
|---|---|---|
| 2010/0231421 A1 | 9/2010 | Rawls-Meehan |
| 2010/0302044 A1 | 12/2010 | Chacon et al. |
| 2010/0317930 A1 | 12/2010 | Oexman et al. |
| 2011/0001622 A1 | 1/2011 | Gentry |
| 2011/0010014 A1 | 1/2011 | Oexman et al. |
| 2011/0015495 A1 | 1/2011 | Dothie et al. |
| 2011/0041592 A1 | 2/2011 | Schmoeller et al. |
| 2011/0068928 A1 | 3/2011 | Riley et al. |
| 2011/0068935 A1 | 3/2011 | Riley et al. |
| 2011/0087113 A1 | 4/2011 | Mack et al. |
| 2011/0094041 A1 | 4/2011 | Rawls-Meehan |
| 2011/0115635 A1 | 5/2011 | Petrovski et al. |
| 2011/0144455 A1* | 6/2011 | Young et al. ............... 600/301 |
| 2011/0156915 A1 | 6/2011 | Brauers et al. |
| 2011/0224510 A1 | 9/2011 | Oakhill |
| 2011/0239374 A1 | 10/2011 | Rawls-Meehan |
| 2011/0252569 A1 | 10/2011 | Rawls-Meehan |
| 2011/0258784 A1 | 10/2011 | Rawls-Meehan |
| 2011/0282216 A1 | 11/2011 | Shinar et al. |
| 2011/0283462 A1 | 11/2011 | Rawls-Meehan |
| 2011/0291795 A1 | 12/2011 | Rawls-Meehan |
| 2011/0291842 A1 | 12/2011 | Oexman |
| 2011/0295083 A1 | 12/2011 | Doelling et al. |
| 2011/0302719 A1 | 12/2011 | Schwirian et al. |
| 2011/0302720 A1 | 12/2011 | Yakam et al. |
| 2011/0306844 A1 | 12/2011 | Young |
| 2012/0025992 A1 | 2/2012 | Tallent et al. |
| 2012/0043475 A1* | 2/2012 | Ahn ..................... 250/453.11 |
| 2012/0053423 A1 | 3/2012 | Kenalty et al. |
| 2012/0053424 A1 | 3/2012 | Kenalty et al. |
| 2012/0056729 A1 | 3/2012 | Rawls-Meehan |
| 2012/0057685 A1 | 3/2012 | Rawls-Meehan |
| 2012/0090698 A1 | 4/2012 | Giori et al. |
| 2012/0110738 A1 | 5/2012 | Rawls-Meehan |
| 2012/0110739 A1 | 5/2012 | Rawls-Meehan |
| 2012/0110740 A1 | 5/2012 | Rawls-Meehan |
| 2012/0112890 A1 | 5/2012 | Rawls-Meehan |
| 2012/0112891 A1 | 5/2012 | Rawls-Meehan |
| 2012/0112892 A1 | 5/2012 | Rawls-Meehan |
| 2012/0116591 A1 | 5/2012 | Rawls-Meehan |
| 2012/0119886 A1 | 5/2012 | Rawls-Meehan |
| 2012/0119887 A1 | 5/2012 | Rawls-Meehan |
| 2012/0138067 A1 | 6/2012 | Rawls-Meehan |
| 2012/0154155 A1 | 6/2012 | Brasch |
| 2012/0186019 A1 | 7/2012 | Rawls-Meehan |
| 2012/0198632 A1 | 8/2012 | Rawls-Meehan |
| 2012/0311790 A1 | 12/2012 | Nomura et al. |
| 2013/0160212 A1 | 6/2013 | Oexman et al. |
| 2013/0174347 A1 | 7/2013 | Oexman et al. |
| 2013/0227787 A1 | 9/2013 | Herbst et al. |
| 2013/0328577 A1* | 12/2013 | Satake et al. ................. 324/688 |
| 2014/0007656 A1 | 1/2014 | Mahoney |
| 2014/0137332 A1 | 5/2014 | McGuire et al. |
| 2014/0182061 A1 | 7/2014 | Zaiss |
| 2014/0250597 A1 | 9/2014 | Chen et al. |
| 2014/0257571 A1 | 9/2014 | Chen et al. |
| 2014/0259417 A1 | 9/2014 | Nunn et al. |
| 2014/0259418 A1 | 9/2014 | Nunn et al. |
| 2014/0259419 A1 | 9/2014 | Stusynski |
| 2014/0259431 A1 | 9/2014 | Fleury |
| 2014/0259433 A1 | 9/2014 | Nunn et al. |
| 2014/0259434 A1 | 9/2014 | Nunn et al. |
| 2014/0277611 A1 | 9/2014 | Nunn et al. |
| 2014/0277778 A1 | 9/2014 | Nunn et al. |
| 2014/0277822 A1 | 9/2014 | Nunn et al. |
| 2014/0313700 A1 | 10/2014 | Connell et al. |
| 2015/0007393 A1 | 1/2015 | Palashewski et al. |
| 2015/0008710 A1 | 1/2015 | Young et al. |
| 2015/0026896 A1 | 1/2015 | Fleury et al. |
| 2015/0136146 A1 | 5/2015 | Hood et al. |
| 2015/0157137 A1 | 6/2015 | Nunn et al. |
| 2015/0157519 A1 | 6/2015 | Stusynski et al. |
| 2015/0182033 A1 | 7/2015 | Brosnan et al. |
| 2015/0182397 A1* | 7/2015 | Palashewski .......... A47C 27/00 5/616 |
| 2015/0182399 A1 | 7/2015 | Palashewski et al. |
| 2015/0182418 A1 | 7/2015 | Zaiss |
| 2015/0290059 A1* | 10/2015 | Brosnan ................ A47C 17/00 5/616 |
| 2015/0374137 A1* | 12/2015 | Mahoney .............. A47C 17/80 5/713 |
| 2016/0100696 A1* | 4/2016 | Palashewski .......... A47C 31/00 700/90 |

OTHER PUBLICATIONS

Takayuki Ishikawa et al.; "A Study on Sleep Stage Estimation via Non-invasive Air Mattress Sensor"; SICE Annual Conference in Fukui, Aug. 4-6, 2003, Fukui University, Japan; pp. 1414-1417.

European Search Report in European Application No. 14826333.8, dated Mar. 11, 2016, 4 pages.

* cited by examiner

DEVICE AND METHOD OF MONITORING A POSITION AND PREDICTING AN EXIT OF A SUBJECT ON OR FROM A SUBSTRATE

FIELD OF THE INVENTION

The present disclosure pertains in general to a monitoring system for monitoring the presence, position, and pattern of movement of a subject on a substrate such as a mattress, and for predicting exit of a subject from the substrate.

BACKGROUND

Monitoring a condition of a subject, such as a subject at rest on a mattress, can include monitoring vital signs, such as heart and respiration rates. Some monitoring systems can include expensive and cumbersome equipment, such as an electrocardiogram (EKG), a ballistocardiograph (BCG), a piezoelectric film, or an array of sensors. EKGs, for example, typically necessitate attaching electrodes in substantially direct contact with a subject, while BCGs rely on large, heavy, unaesthetic force-measuring platforms.

In some implementations, monitoring a condition of a subject can include monitoring the presence or absence of a subject, for example, the presence or absence of a subject on a mattress. However, in addition to being expensive and cumbersome, monitoring systems can be unable to accurately predict when a subject is about to change condition, for example, when a presence condition is about to change from present to absent base on the subject exiting the mattress.

SUMMARY

Methods and devices for monitoring a position of a subject on a substrate are disclosed. One such method includes sensing incident pressure waves generated by the subject moving on a divided bladder comprising interleaved portions with at least one sensor in fluid communication with a respective portion of the divided bladder, generating signals indicative of the incident pressure waves for each of the interleaved portions of the bladder and sending the signals to a processor, determining a position of the subject on the divided bladder based on a difference between the signals from each of the interleaved portions and generating a position pattern for the subject over a period of time.

Another method includes sensing, with one or more sensors, incident pressure waves generated by the subject moving on a divided bladder comprising interleaved portions wherein the one or more sensors are in fluid communication with the bladder; generating signals indicative of the incident pressure waves for each of the interleaved portions of the bladder and sending the signals to a processor; determining the presence of the subject on the divided bladder based on the magnitude of the signals from each of the interleaved portions; determining the position of the subject on the divided bladder based on the difference between the signals from each of the interleaved portions; generating a pattern for the subject, wherein the pattern includes the presence and position of the subject over time; and predicting an exit of the subject from the divided bladder based on comparing a current pattern for the subject to previous patterns for the subject.

In another embodiment, a non-intrusive monitoring device for monitoring the position of a subject is disclosed. The device includes a divided bladder comprising interleaved portions; one or more sensors in fluid communication with the interleaved portions of the divided bladder wherein the one or more sensors are configured to generate signals in response to pressure variations resulting from movement of a subject on the divided bladder; and a processor. The processor is configured to: receive signals from the one or more sensors for each of the interleaved portions; determine the subject's presence on the divided bladder based on the magnitude of the signals from each of the interleaved portions; determine the subject's position on the divided bladder based on the difference between the signals from each of the interleaved portions; generate a pattern for the subject, wherein the pattern includes the subject's presence and subject's position over time; and predict an exit of the subject from the divided bladder based on comparing a current pattern for the subject to previous patterns for the subject.

In another embodiment, a device for monitoring the position of a subject on a substrate is disclosed. The device includes: a sensing unit having a divided bladder comprising interleaved portions configured to be placed under the substrate on which the subject lies and one or more sensors in fluid communication with the interleaved portions, wherein the one or more sensors are configured to sense pressure variations within the divided bladder generated by movement of the subject and to generate signals indicative of the pressure variations; a processor configured to receive the signals and to determine and generate output indicative of the subject's position based on the difference between the signals from each of the interleaved portions; and an external device configured to display the output.

BRIEF DESCRIPTION OF THE DRAWINGS

The description makes reference to the accompanying drawings, wherein like reference numerals refer to like parts throughout the several views, and wherein.

DETAILED DESCRIPTION

Method and devices for non-intrusive monitoring of the position and presence of a subject on a substrate such as a mattress are disclosed here. Unlike monitors that are placed in substantially direct contact with a subject, such as monitors that include electrodes, pressure cuffs, and the like, non-intrusive monitoring, such as the method and apparatus described here, can monitor a condition of a subject without being in substantially direct contact with the subject. A non-intrusive monitoring apparatus, or one or more portions thereof, can be transported for use by a subject to different locations. Non-intrusive monitoring can include detecting, storing, processing, and communicating information indicating a condition of a subject. For example, a non-intrusive monitoring apparatus can detect condition information, such as presence, position, and pattern of movement of the subject over time, and can communicate the condition information to a monitoring controller that can receive, store, process, and present the condition information, related information, or both, via, for example, an audio or video display device.

The position of a subject can be the location of the subject on a substrate such as a bed. In addition to the location, the position can include the configuration of the subject's head, torso, legs and feet using heart rate and respiration rate, for example, in addition to center of mass and other pressure measurements. The position can also include whether the subject is lying on his or her right or left side based on heart rate and /or respiration. The position can also include whether the subject is lying down, partially reclining or sitting on the substate.

Figure 1:
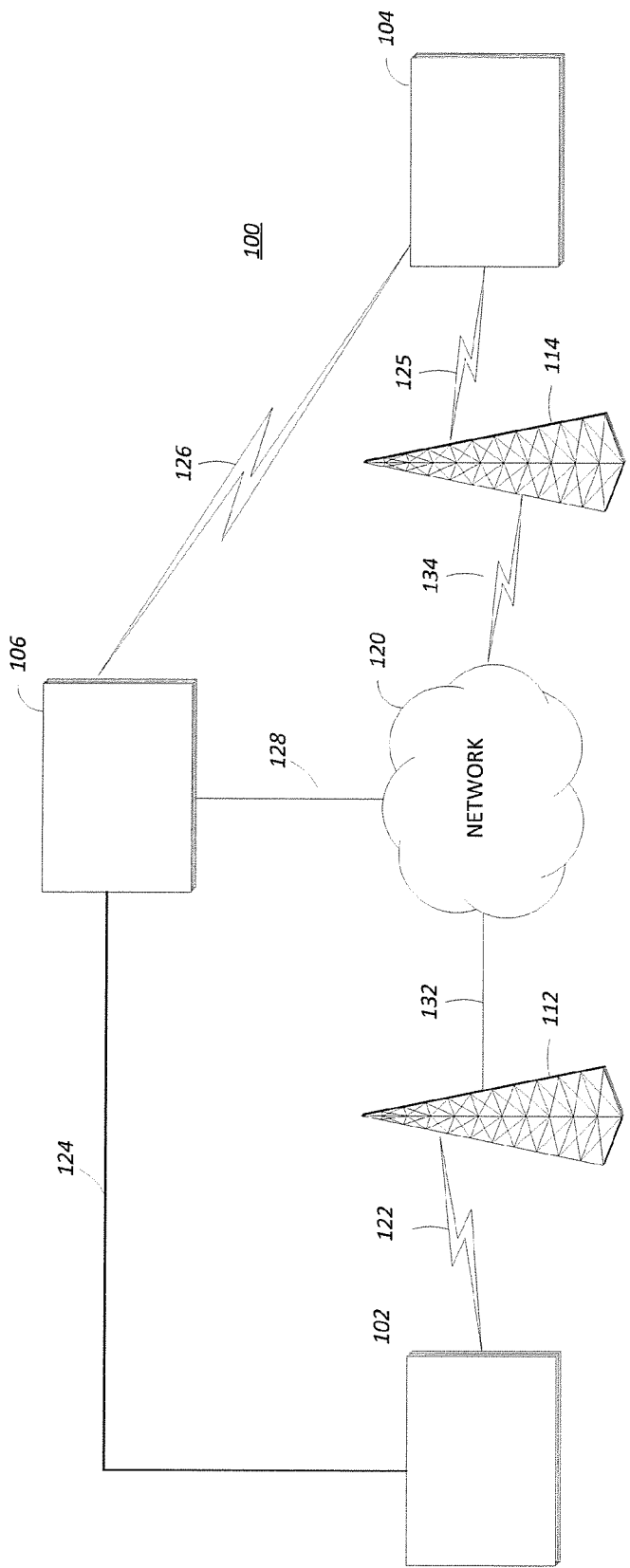
FIG. 1 is a diagram of a computing and communications system in accordance with implementations of this disclosure.

FIG. 1 is a diagram of a computing and communications system 100 in accordance with implementations of this disclosure. The computing and communications system 100 can include one or more computing and communication devices 102/104/106, one or more access points 112/114, one or more networks 120, or a combination thereof. Although shown here as including three computing and communication devices 102/104/106, two access points 112/114, and one network 120, the computing and communications system 100 can include any number of computing and communication devices, access points, and networks.

A computing and communication device 102/104/106 can be any device or system configured to perform wired or wireless communication. For example, a computing and communication device 102 can be configured to perform wireless communication via a wireless communication link 122, via a wired communication link 124, or both. In another example, a computing and communication device 104 can be configured to perform wireless communication via a first wireless communication link 125, via a second wireless communication link 126, or both. In another example, a computing and communication device 106 can be configured to perform wired communication via a first wired communication link 124, can be configured to perform wireless communication via a wireless communication link 126, can be configured to perform wired communication via a second wired communication link 128, or can be configured to communicate via a combination of wired and wireless communication links 124/126/128.

The computing and communication devices 102/104/106 can communicate with each other directly via a wired or wireless communication link 124/126, indirectly via an access point, indirectly via the network 120 using one or more a wired or wireless communication links, or via a combination of wired and wireless communication links 122/124/125/126/128. Although each computing and communication device 102/104/106 is shown as a single unit, a computing and communication device can include any number of interconnected elements.

An access point 112/114 can be any type of device configured to communicate with a computing and communication device 102/104/106, a network 120, or both, via wired or wireless communication links 122/124/125/126/128. For example, an access point 112/114 can include a base station, a base transceiver station (BTS), a Node-B, an enhanced Node-B (eNode-B), a Home Node-B (HNode-B), a wireless router, a wired router, a hub, a relay, a switch, or any similar wired or wireless device. An access point 112/114 can communicate with the network 120 via a wired communication link 132, a wireless communication link 134, or a combination of wired and wireless communication links. Although each access point 112/114 is shown as a single unit, an access point can include any number of interconnected elements.

The network 120 can be any type of network configured to provide services, such as voice, data, or any other communications protocol or combination of communications protocols, over a wired or wireless communication link. For example, the network 120 can be a local area network (LAN), wide area network (WAN), virtual private network (VPN), a mobile or cellular telephone network, the Internet, or any other means of electronic communication. The network can use a communication protocol, such as the transmission control protocol (TCP), the user datagram protocol (UDP), the internet protocol (IP), the real-time transport protocol (RTP) the Hyper Text Transport Protocol (HTTP), or a combination thereof.

Figure 2:
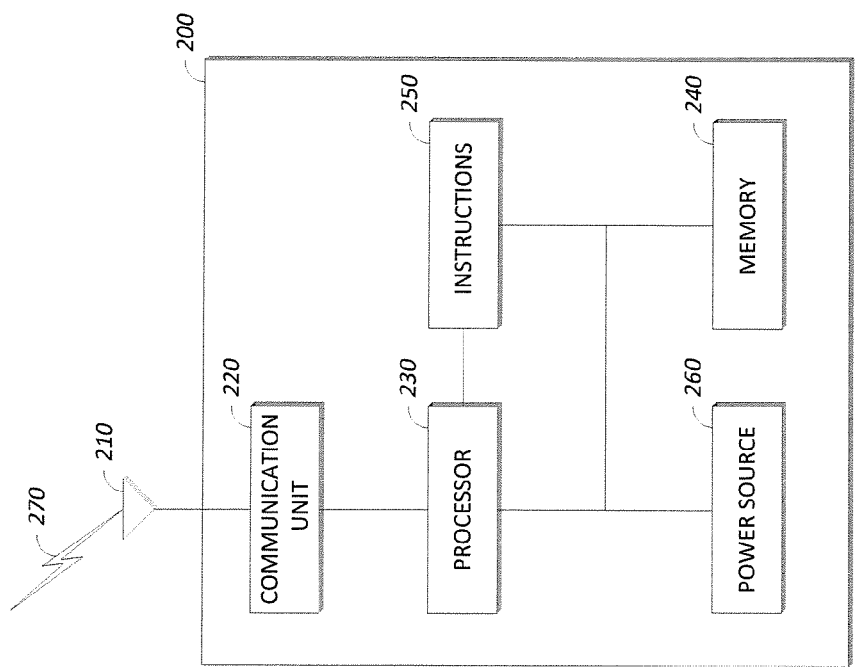
FIG. 2 is a diagram of an example computing and communication device in accordance with implementations of this disclosure.

FIG. 2 is a diagram of an exemplary computing and communication device 200 in accordance with implementations of this disclosure. For example, each of the computing and communication devices 102/104/106 shown in FIG. 2 can be a computing and communication device 200 as shown in FIG. 2. A computing and communication device 200 can include a communication interface 210, a communication unit 220, a processor 230, a memory 240, instructions 250, a power source 260, or any combination thereof. As used herein, the term "computing device" includes any unit, or combination of units, capable of performing any method, or any portion or portions thereof, disclosed herein.

The computing and communication device 200 can be a stationary computing device or a mobile computing device. For example, the computing and communication device 200 can be a personal computer (PC), a server, a workstation, a minicomputer, a mainframe computer, a mobile telephone, a personal digital assistant (PDA), a laptop, a tablet PC, or an integrated circuit. Although shown as a single unit, any one or more elements of the communication device 200 can be integrated into any number of separate physical units.

The communication interface 210 can be a wireless antenna, as shown, a wired communication port, such as an Ethernet port, an infrared port, a serial port, or any other wired or wireless unit capable of interfacing with a wired or wireless communication medium 270. The communication unit 220 can be configured to transmit or receive signals via a wired or wireless communication medium 270, such as radio frequency (RF), ultra violet (UV), visible light, fiber optic, wire line, or a combination thereof. Although FIG. 2 shows a single communication unit 220 and a single communication interface 210, any number of communication units and any number of communication interfaces can be used.

The processor 230 can include any device or system capable of manipulating or processing a signal or other information, such as optical processors, quantum processors, molecular processors, or a combination thereof. For example, the processor 230 can include a general purpose processor, a special purpose processor, a conventional processor, a digital signal processor (DSP), a plurality of microprocessors, one or more microprocessor in association with a DSP core, a controller, a micro controller, an Application Specific Integrated Circuit (ASIC), a Field Programmable Gate Array (FPGA), a programmable logic array, programmable logic controller, microcode, firmware, any type of integrated circuit (IC), a state machine, or any combination thereof. As used herein, the term "processor" includes a single processor or multiple processors. The processor can be operatively coupled with the communication unit 220, the memory 240, the instructions 250, the power source 260, or any combination thereof.

The memory 240 can include any non-transitory computer-usable or computer-readable medium, such as any tangible device that can, for example, contain, store, communicate, or transport the instructions 250, or any information associated therewith, for use by or in connection with the processor 230. The non-transitory computer-usable or computer-readable medium can be, for example, a solid state drive, a memory card, removable media, a read only memory (ROM), a random access memory (RAM), any type of disk including a hard disk, a floppy disk, an optical disk, a magnetic or optical card, an application specific integrated circuits (ASICs), or any type of non-transitory media suitable for storing electronic information, or any combination thereof. The memory 240 can be connected to, for example, the processor 230 through, for example, a memory bus (not explicitly shown).

The instructions 250 can include directions for performing any method, or any portion or portions thereof, disclosed here. The instructions 250 can be implemented in hardware, software, or any combination thereof. For example, the instructions 250 can be implemented as information stored in the memory 240, such as a computer program, that can be executed by the processor 230 to perform any of the respective methods, algorithms, aspects, or combinations thereof, as described here. The instructions 250, or a portion thereof, can be implemented as a special purpose processor, or circuitry, that can include specialized hardware for carrying out any of the methods, algorithms, aspects, or combinations thereof, as described herein. Portions of the instructions 250 can be distributed across multiple processors on the same machine or different machines or across a network such as a local area network, a wide area network, the Internet, or a combination thereof.

The power source 260 can be any suitable device for powering the computing and communication device 200. For example, the power source 260 can include a wired power source; one or more dry cell batteries, such as nickel-cadmium (NiCd), nickel-zinc (NiZn), nickel metal hydride (NiMH), lithium-ion (Li-ion); solar cells; fuel cells; or any other device capable of powering the communication device 200. The communication interface 210, the communication unit 220, the processor 230, the instructions 250, the memory 240, or any combination thereof, can be operatively coupled with the power source 260.

Although not shown in FIG. 2, in some embodiments, the computing and communication device 200 can include a user interface (UI), which can be any unit capable of interfacing with a user, such as a virtual or physical keypad, a touchpad, a display, a touch display, a speaker, a microphone, a video camera, a sensor, or any combination thereof. The UI can be operatively coupled with the processor, as shown, or with any other element of the computing and communication device 200, such as the power source 260. Although shown as a single unit, the UI can include one or more physical units. For example, the UI can include an audio interface for performing audio communication with a user, and a touch display for performing visual and touch based communication with the user.

FIG. 2 shows one exemplary configuration of a computing and communication device 200 and is not meant to imply limitations with respect to the embodiments. Other elements can be used in addition to or in the place of the depicted elements, and the computing and communication device 200 can be implemented on a variety of hardware platforms and software environments, such as various operating systems. Although shown as separate elements, the communication interface 210, the communication unit 220, the processor 230, the instructions 250, the power source 260, the memory 240, the UI, or any combination thereof can be integrated in one or more electronic units, circuits, or chips.

Figure 3:
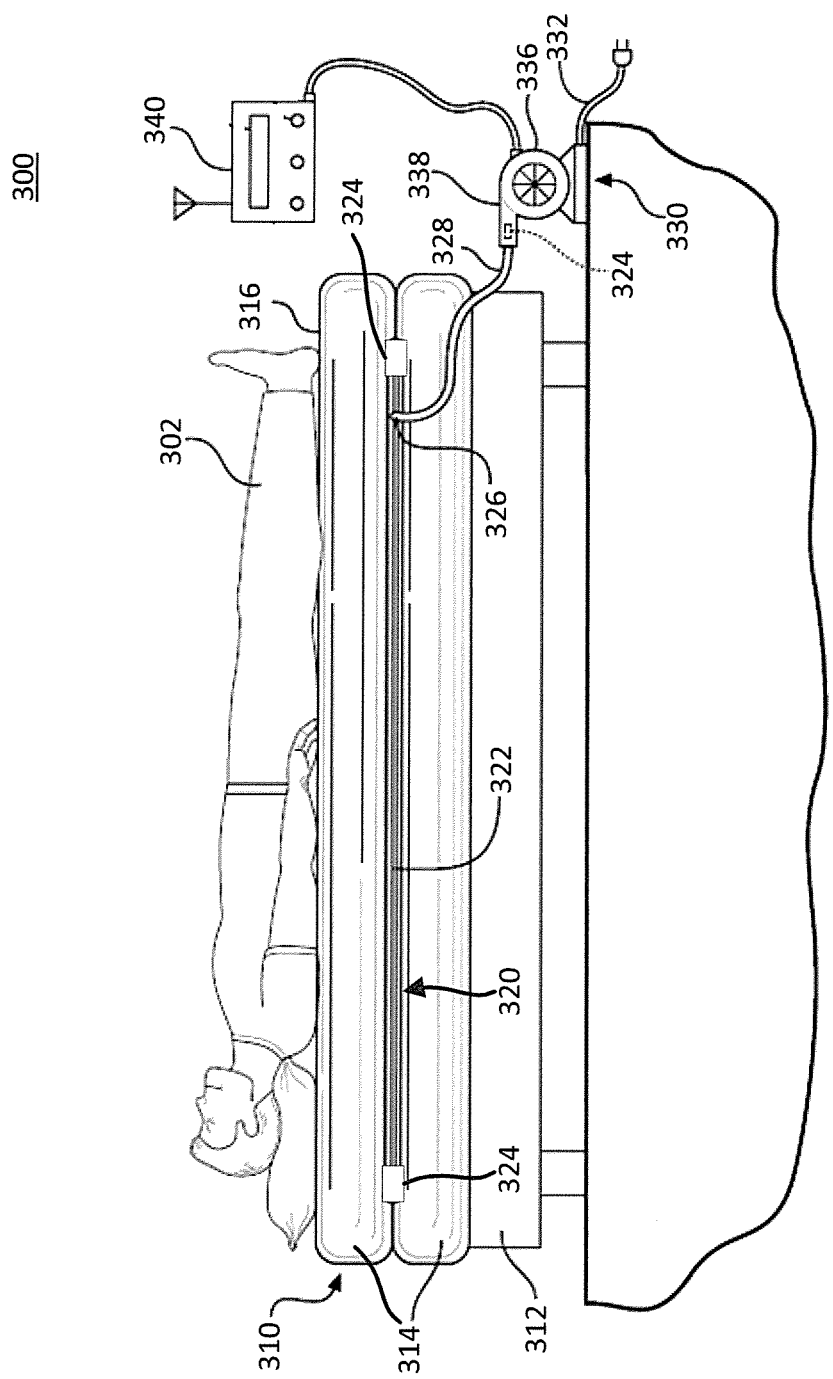
FIG. 3 shows an example of a non-intrusive monitoring apparatus for monitoring a condition of a subject in accordance with implementations of this disclosure.

FIG. 3 shows an example of a non-intrusive monitoring apparatus 300 for monitoring a condition of a subject 302 in accordance with this disclosure. In some embodiments, the non-intrusive monitoring apparatus 300 can be used in conjunction with a substrate, such as bed 310. As shown in FIG. 3, a subject 302 can be positioned on the bed 310 such that the non-intrusive monitoring apparatus 300 can detect an action or condition, such as movement, a position or a vital sign, of the subject 302. For example, the subject 302 can be resting in a reclined position on the bed 310 above at least a portion of the non-intrusive monitoring apparatus 300, as shown. In some embodiments, the non-intrusive monitoring apparatus 300 can be configured to concurrently detect multiple conditions of the subject 302. For example, the non-intrusive monitoring apparatus 300 can concurrently detect a heart rate, a respiration rate, a position of and movement of the subject 302.

In some embodiments, the bed 310 can include a frame 312 and one or more padding layers 314. The padding layers 314 can include one or more of a foam pad, a box spring, a mattress, an additional bladder, an air bladder, a straw-filled pad, a feather-filled pad, a sawdust-filled pad, a spring-based pad, or any padding layer capable of supporting the subject 302 and at least a portion of the non-intrusive monitoring apparatus 300. The bed 310 can have a top surface area 316, such as a surface area of a top side of a mattress.

In some embodiments, the non-intrusive monitoring apparatus 300 can include a monitoring unit 320, a pump 330, a monitoring controller 340, or any combination thereof. The monitoring unit 320, the pump 330, and the monitoring controller 340 can be configured as separate units as shown, or as one or more combined units. For example, the monitoring unit 320 can be configured as a first unit and the pump 330 and the monitoring controller 340 can be configured as a second combined unit, separate from the monitoring unit 320. In another example, the monitoring unit 320, the pump 330, and the monitoring controller 340 can be configured as single combined unit.

In some embodiments, the monitoring unit 320, or a portion thereof, can be removably positioned on a single padding layer or between two padding layers 314 of the bed as shown. In some embodiments, the bed 310 can include one or more padding layers 314 and the non-intrusive monitoring apparatus 300 can include one or more additional padding layers (not shown). In some embodiments, the monitoring unit 320 can be fixedly attached to one or more padding layers. In some embodiments, the monitoring unit 320 can include one or more bladders 322, one or more sensors 324, one or more inlets 326, or any combination thereof.

In some embodiments, the bladder 322 can be configured to contain a fluid, such as air, water, or any other appropriate fluid. In some embodiments, the bladder 322 will have foam to self-inflate the bladder 322 and eliminate the need for a pump 330. The bladder 322 can be sized to have a surface area substantially as large as the surface area of the bed 310. For example, the bladder 322 can have a surface area substantially as large as a king-size, queen-size, full, twin, or other sized mattress. Although described as having a surface area that is substantially as large as the surface area of the bed 310, the bladder 322 can be of any size capable of detecting a position of the subject 302 on the bed 310. For example, the surface area of the bladder 322 can be substantially smaller than the surface area 316 of the bed 310. In some embodiments, the bladder 322 can be configured for use in a chair, automobile seat, hospital bed, crib, or other structure capable of supporting a subject.

The pressure in the bladder 322 can vary depending on the amount of fluid in the bladder 322, whether the subject 302 is lying on the bladder 322 or sitting on the bladder 322, the heart rate of the subject 302 lying on the bladder 322, the respiration rate of the subject 302 lying on the bladder 322, or other movement of the subject 302 lying on the bladder 322. As used herein the term 'unladened reference pressure' can indicate an average fluid pressure within the bladder 322 in the absence of a subject 302 over a period of time, and the term ladened reference pressure' can indicate an average fluid pressure within the bladder 322 in the presence of a subject 302 over a period of time. For simplicity, the term 'reference pressure' can indicate the ladended or unladened reference pressure.

In some embodiments, one or more sensors 324 can be configured to detect and measure changes in pressure, incident pressure waves, or both, within the bladder 322. For example, incident pressure waves caused by shifting body weight in response to cardiopulmonary activity can induce a change in pressure that can be detected and measured by the sensors 324. In some embodiments, a sensor 324 can be positioned such that the sensor 324 has a sensing side within the bladder 322 and a reference side outside of the bladder 322. The sensor 324 can include a pressure sensor, such as a semiconductor pressure sensor. In some embodiments, the sensor 324 can include other types of sensors, such as a temperature sensor. The sensor 324 can output a pressure signal indicating measured changes of the pressure in the bladder 322.

For example, the one or more sensors 324 can include a computing and communication device, such as the computing and communication devices 102/104/106 shown in FIG. 1 or the computing and communication device 200 shown in FIG. 2, and can be configured to output pressure signals to the pump 330, the monitoring controller 340, to an external device (not shown), or to any combination thereof, via a wired or wireless communication link. In some embodiments, the sensors 324 can be configured to receive and respond to control signals from the monitoring controller 340, an external device, or both. In some embodiments, the sensors 324 can be configured to condition the pressure signals, which can include amplifying and filtering the pressure signal. For example, the sensors 324 can be configured to generate a pressure signal by measuring the fluid pressure, to condition the pressure signal, and to send the conditioned pressure signal to the pump 330, the monitoring controller 340, an external device, or any combination thereof.

In some embodiments, the inlet 326 can be configured to provide fluid communication between the bladder 322 and the pump 330. For example, the inlet 326 can be integrated with the bladder 322 and can fluidly communicate with pump 330 via a hose 328 as shown. In another example, the pump 330 can be integrated with the bladder 322 and the hose 328 can be omitted.

In some embodiments, the non-intrusive monitoring apparatus 300 can include the pump 330, which can be a rotary pump or any other type of pump, configured to maintain a reference or average pressure within the bladder 322. The pump 330 can include an electric line 332 for connection to a power source, the pump 330 can include a self-contained power source, such as one or more batteries, or the pump 330 can include an electric line and a self-contained power source. In some embodiments, the non-intrusive monitoring apparatus 300 can include a self-inflating bladder and the pump 330 can be omitted.

In some embodiments, the pump 330 can include a sensor 334. For example, a pump housing 336 can provide a casing containing components of the pump 330 and can contain the sensor 334. For example, the sensor 334 can be positioned in a portion of the pump 330 in fluid communication with the hose 328, via, for example, a pressurized fluid outlet 338 of the pump 330. The pressure of the hose 328, which can be in fluid communication with the bladder 322, can correspond to the pressure in the bladder 322. The pump 330, the sensor 334, or both, can be configured for wired or wireless communication. For example, the pump 330 can include a computing and communication device, such as the computing and communication devices 102/104/106 shown in FIG. 1 or the computing and communication device 200 shown in FIG. 2, and can be configured to communicate with the sensors 324, the monitoring controller 340, an external device (not shown), or with a combination thereof, via a wired or wireless communication link. For example, the pump 330 can be configured to receive the pressure signal from the sensors 324, to condition the pressure signal, and to send the pressure signal to the monitoring controller 340, to an external device (not shown), or to any combination thereof, via a wired or wireless communication link. In some embodiments, the pump 330, the sensor 334, or both, can be configured to receive and respond to control signals from the monitoring controller 340, an external device, or both.

In some embodiments, the non-intrusive monitoring apparatus 300 can include a monitoring controller 340. The monitoring controller 340 can be a computing and communication device, such as the computing and communication devices 102/104/106 shown in FIG. 1 or the computing and communication device 200 shown in FIG. 2, can be configured to communicate with the sensors 324, the pump 330, an external device (not shown), or with a combination thereof, via a wired or wireless communication link, and can be configured to control the non-intrusive monitoring apparatus 300. For example, the monitoring controller 340 can receive a signal indicating the pressure of the bladder 322 and can control the pump 330 to maintain or increase the reference pressure in the bladder 322.

In some embodiments, the bladder 322, the pump 330, or both, can include a pressure release unit, such as a pressure release valve, configured for releasing pressure in the bladder 322, and the monitoring controller 340 can be configured to control the pressure release unit to decrease the fluid pressure in the bladder 322. In some embodiments, the pressure release unit can include a computing and communication device, such as the computing and communication devices 102/104/106 shown in FIG. 1 or the computing and communication device 200 shown in FIG. 2, and can be configured to communicate with the sensors 324, the pump 330, the monitoring controller 340, an external device (not shown), or with a combination thereof, via a wired or wireless communication link.

In an example, the monitoring controller 340 can analyze the pressure signal and can convert it to one or more parameters associated with the subject 302. The parameters can include, but are not limited to, a heart rate, a respiration rate, a change in position, a change in static pressure, or changes in differential pressure between multiple bladders. The parameters can be analyzed to determine a condition of the subject 302, such as a length of sleep, a quality of sleep, a position, a presence or absence in the bed, a blood pressure, tossing and turning movements, rolling movements, limb movements, weight, a predictive exit from the bladder, or other conditions. For example, the subject 302 can rest against the bladder 322 either directly, or indirectly, via one or more padding layers 314, and each of the subject's heart beats, breaths, and other movements can create a force on the bladder 322 that can be transmitted to one or more sensors 324 each as a wave propagated through the fluid of a different strength and frequency. The one or more sensors 324 can detect the wave, and can generate a corresponding pressure signal a that can be computed into data such as a heart rate, respiratory rate, position change, or other parameter regarding the subject 302.

In some embodiments, detected pressure signals, parameters, condition information, or a combination thereof, can be stored and analyzed in combination to refine the information or to generate additional information regarding the subject 302. For example, information can be used to generate a unique biological pattern for the subject 302, which can include a combination of heart beat, respiration, weight, static pressure, patterns of position change, or a combination thereof. In one example, the apparatus 300 can determine that an isolated change in pressure, such as a change in pressure caused by placing a heavy static object, such as a suitcase, on the bed 310, was not caused by the subject 302. In another example, information indicating a change in pressure caused by the arrival of the subject 302, such as the subject 302 sitting on the bed, can be combined with the unique heart beat and respiration of the subject 302 to determine if that particular subject 302 is resting on the monitoring unit 320. In some embodiments, the non-intrusive monitoring apparatus 300 can determine changes in position of the subject 302 based on the information. For example, the non-intrusive monitoring apparatus 300 can determine that a subject 302 is lying down flat based on strong heart beat and respiration signals, and the non-intrusive monitoring apparatus 300 can determine that the subject 302 is lying on his or her left side or right side. For example, if the heart beat signal is weak and the respiration signal is strong, the subject 302 is lying on the right side.

The monitoring controller 340 can receive the conditioned pressure signal from the sensors 324 and can perform pattern recognition, or other calculations, based on the conditioned pressure signal to determine the position, heart rate, respiratory rate, or other bio-signal properties or conditions associated with the subject 302. For example, the heart rate can be identified based on a portion of the signal that has a frequency in the range of 0.5-4.0 Hz and the respiration rate can be identified based on a portion of the signal has a frequency in the range of less than 1 Hz. The monitoring controller 340 can also receive signals from other sensors, such as a temperature sensor. The monitoring controller 340 can receive and process signals from a plurality of sensors 324 in a non-intrusive monitoring apparatus 300, or from different non-intrusive monitoring apparatuses in use by different subjects.

The monitoring controller 340 can send information, such as information indicating the parameters of the subject, such as the position, heart rate, and respiratory rate, to an external device, which can be accessible to a user, such as a text messaging platform, a data logger, a printer, an alarm system, an alert siren, or other data acquisition or actuating device, or a computer capable of performing analytical functions.

Medical facilities such as hospitals, nursing homes and psychiatric institutions can use the non-intrusive monitoring apparatus 300 for many different reasons. A medical facility might use the non-intrusive monitoring apparatus 300 in each bed, or each bed of a ward or floor, with each subject 302 or patient associated with a non-intrusive monitoring apparatus 300 or bed, providing instant information to the user of which beds include patients, which beds are available to new patients, what position each patient currently has in each bed, which patients are moving in their beds, etc. Because the non-intrusive monitoring apparatus 300 is a non-contact monitoring system, patients need not be "hooked up" to the apparatus. The system does not need to be turned on by an employee or otherwise initiated. The system can begin to monitor the patient as soon as the patient rests against the bladder 322.

There are additional uses for the non-intrusive monitoring apparatus 300 in medical facilities. Non-limiting examples include providing a current and historical account of patient vital signs such as respiration and heart rate to caregivers and providing a current and historical account of patient motion to prevent bed sores, presence in bed, or absence from bed. In addition, the non-intrusive monitoring apparatus 300 can be configured to predict when a patient will exit a bed based on the pressure pattern of the patient's position sensed with reference to the edges of the bed, for example, and indications of directional motion of the patient sensed before a patient's absence. An example monitoring unit 320 configured for use in pinpointing patient position and detecting direction of patient motion is described with reference to FIG. 4 below.

Figures 4A, 4B:
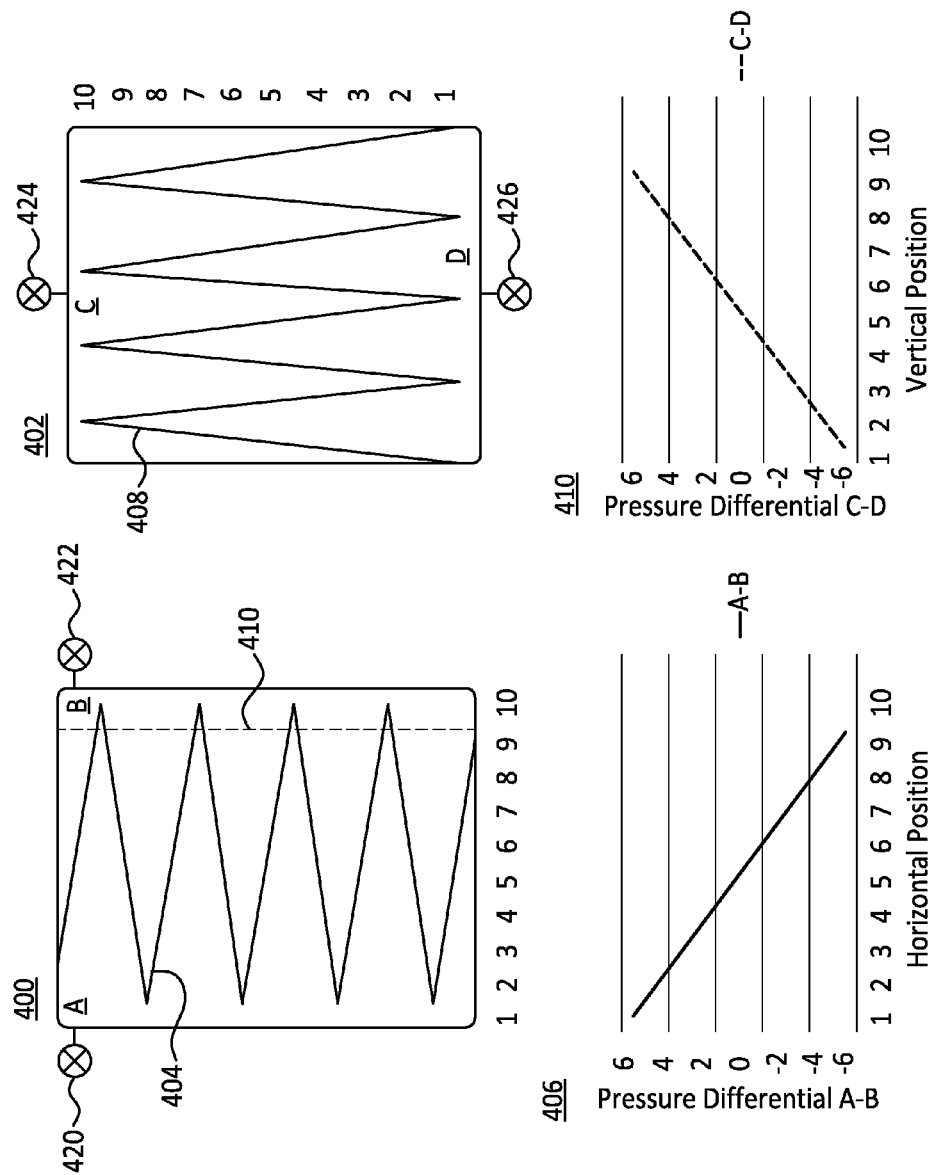
FIGS. 4A and 4B show a top view of a pair of seamed bladders for monitoring a position of a subject using the apparatus of FIG. 3 and graphical representations of pressure differentials along the seamed bladders by subject position.

FIGS. 4A and 4B show a top view of a pair of bladders 400/402 for monitoring a position of a subject 302 using the non-intrusive monitoring apparatus 300 of FIG. 3. The pair of bladders 400/402 can be stacked one on top of the other and positioned on top of, below, or between padding layers, for example, between padding layers 314 in a similar position to bladder 322 in FIG. 3. The bladder 400 of FIG. 4A includes a horizontal seam 404 separating the bladder 400 into two portions A/B. The seam 404 can be created by any means known to those skilled in the art. The horizontal seam 404 creates a horizontal zig-zag pattern on the bladder 400, splitting the bladder 400 into the two portions A/B. In the example shown here, portion A includes fingers, or teeth, that extend between the fingers, or teeth, of portion B. Though the fingers or teeth shown in FIG. 4A are triangular, they can also be in any other shape. The design is configured such that the portions A/B are interleaved, allowing each portion A/B to sense position in a linear manner. Though each of the portions A/B shown in FIG. 4A includes approximately half of the bladder 400, the horizontal seam 404 can also be configured to divide the bladder 400 into quarters, eights, sixteenths, or unequally sectioned portions.

By separating the bladder 400 into interleaved portions A/B, the pressure can be measured independently in each portion A/B. The seam 404 is configured so that each interleaved portion A/B extends nearly the entire width of the bladder 400. This allows for each interleaved portion A/B to have some degree of pressure exerted on it by the subject at nearly any location on the bladder 400, as opposed to a vertical seam creating portions that are not interleaved. This degree of pressure can be interpreted based on the amount or percentage of the portion to which the subject is exposed when compared to the degree of pressure on the other interleaved portion.

In one example, the bladder 400 can include or be in communication with one or more pressure sensors 420/422. The one or more pressure sensors 420/422 can be configured to measure the pressure both in portion A and portion B. The sensors 420/422 can be positioned at any location along the portion the sensors 420/422 will be measuring. The pressure in portion A will increase linearly as a subject, e.g. subject 302 shown in FIG. 3, moves toward the left side of the bladder 400. In a similar manner, the pressure in portion B will increase linearly as the subject 302 moves toward the right side of the bladder 400.

The difference in pressure between portion A and portion B can be used to represent the horizontal position of, for example, the subject 302 reclining or sitting on a substrate such as a bed or mattress including the bladder 400. FIGS. 4A and 4B also show graphical representations of pressure differentials along the seamed bladders 400/402 by subject 302 position. In graph 406, the horizontal position of a subject 302 is shown along the x-axis. This horizontal position is represented using horizontal indicators, 1-10, shown both below the bladder 400 and on the x-axis label of the graph 406. An example normalized linear representation of the pressure differential, that is, the pressure of portion A minus the pressure of portion B, for a subject 302 moving from the left side to the right side of the bladder 400 is shown along the y-axis.

For example, if a subject 302 has a center of mass located at the horizontal position denoted by '3' both on the bladder 400 and on the graph 406, the pressure differential between the portions, e.g. pressure of portion A minus pressure of portion B, would also be approximately '3.' If a subject 302 has a center of mass located at the horizontal position denoted by '8' both on the bladder 400 and on the graph 406, the pressure differential between the portions would be approximately '−4.' Thus, by calculating the pressure differential between the portions A/B of the bladder 400, the horizontal position of the subject 302 can be predicted.

The pressure differential between the portions A/B of the bladder 400 can provide predictive capabilities of a subject's action based on movement, such as exit from the bladder. By capturing a string, or stream, of pressure differentials while the subject 302 moves along the bladder 400, the horizontal direction of motion of the subject 302 is determined. From the position pattern, including one or both of speed of movement and trajectory of movement, as examples, an action of the subject can be predicted. For example, if the trajectory is toward an edge of the bed in which the bladder 400 is incorporated, an action such as exit of the bed can be predicted. This prediction can trigger an indication or alarm to a caregiver that the subject is about to exit the bed, calling the caregiver to the subject to assist in the exit and getting to the desired location without falling. The predication can trigger a reminder or alarm for the subject. For example, a verbal warning may be triggered for the subject to call a nurse for assistance before getting out of bed.

If the stream of pressure differentials is followed by a subsequent absence of the subject 302 from the substrate, the representative pressure differentials can be stored, for example, in the memory 240 of the computing and communication device 200 shown in FIG. 2, and associated as a position pattern of pressure differentials indicative of the subject 302 being about to exit the bed or mattress. The historical position pattern data can be used to assist in predicting the action of the subject. For example, if the subject always gets out of bed on the same side, but the current trajectory of the position pattern is toward the opposite side, an action such as exiting the bed may not be predicted. If the subject always pauses in a sitting position before exiting, the center of mass near the edge of the bed can trigger a prediction of bed exit. If the same, or similar, string or pattern of pressure differentials is captured, an alert or an alarm can be sent to a caregiver to indicate that the subject 302 might be about to exit the bed or mattress. This can prevent falls, which is a serious problem in medical facilities.

The bladder 402 shown in FIG. 4B includes a vertical seam 408 separating the bladder 402 into two portions C/D. The vertical seam 408 creates a vertical zig-zag pattern on the bladder 402, splitting the bladder 402 into the two portions C/D. In the example shown here, portion C includes fingers, or teeth, that extend between the fingers, or teeth, of portion D. The seam 408 is configured so that each interleaved portion C/D extends nearly the entire length of the bladder 402. This allows for each interleaved portion C/D to have some pressure exerted on it by the subject at nearly any location on the bladder 402, as opposed to a horizontal seam creating portions that are not interleaved. Though the fingers or teeth shown in FIG. 4B are triangular, they can also be in any other shape. Further, though each of the portions C/D shown in FIG. 4B includes approximately half of the bladder 402, the vertical seam 408 can also be configured to divide the bladder 402 into quarters, eights, sixteenths, or unequally sectioned portions.

In a similar manner as described with respect to bladder 400, the pressure can be measured independently in each portion C/D of the bladder 402 with pressure sensors 424/426. The sensors 424/426 can be positioned at any location along the portions that the sensors 424/426 will be measuring. The pressure in portion C will increase linearly as a subject, e.g. subject 302 shown in FIG. 3, moves toward the top of the bladder 402. In a similar manner, the pressure in portion D will increase linearly as the subject 302 moves toward the bottom of the bladder 402.

The difference in pressure between portion C and portion D can be used to represent the vertical position of, for example, the subject 302 reclining or sitting on a substrate such as a bed or mattress including the bladder 402. In graph 410, the vertical position of a subject 302 is shown along the x-axis. This vertical position is represented using vertical indicators, 1-10, shown both on the side of the bladder 402 and on the x-axis label of the graph 410. An example normalized linear representation of the pressure differential, that is, the pressure of portion C minus the pressure of portion D, for a subject 302 moving from the bottom to the top of the bladder 402 is shown along the y-axis.

For example, if a subject 302 has a center of mass located at the vertical position denoted by '3' both on the bladder 402 and on the graph 410, the pressure differential between the portions, e.g. portion C minus portion D, would be approximately '−4.' If a subject 302 has a center of mass located at the vertical position denoted by '8' both on the bladder 402 and on the graph 410, the pressure differential between the portions would be approximately '4.' Thus, by calculating the pressure differential between the portions C/D of the bladder 402, the vertical position of the subject 302 can be predicted. In the same manner as was described with respect to horizontal motion and prediction in reference to bladder 400 and graph 406, pressure differentials between portions C/D can be used to determine the path of vertical motion and predict when a subject 302 is about to exit the substrate, e.g. the bed or mattress.

The bladders 400/402 shown in FIGS. 4A and 4B can be stacked together, one on top of the other, to provide a center of mass for the subject 302 based on both horizontal and vertical position as determined by the pressure differentials between portions A/B of bladder 400 and portions C/D of bladder 402. Also, both horizontal motion and vertical motion of a subject 302 can be captured and stored before and after an exit event for use in further prediction if both bladders 400/402 are used at the same time with the non-intrusive monitoring apparatus 300. Example subject 302 positions based on stacking of the bladders 400/402 are described in respect to FIGS. 5A-5C.

Figure 5C:
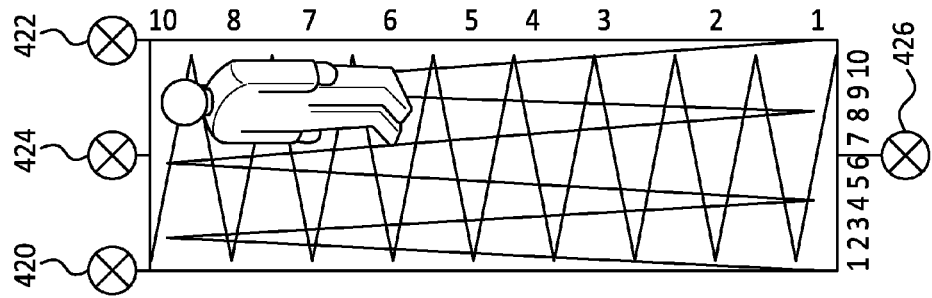
FIGS. 5A-5C illustrate the non-intrusive monitoring apparatus used in monitoring a subject's position.
Figure 5B:
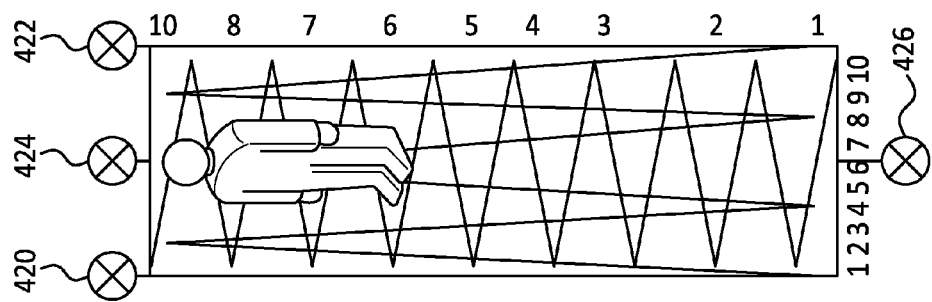
Figure 5A:
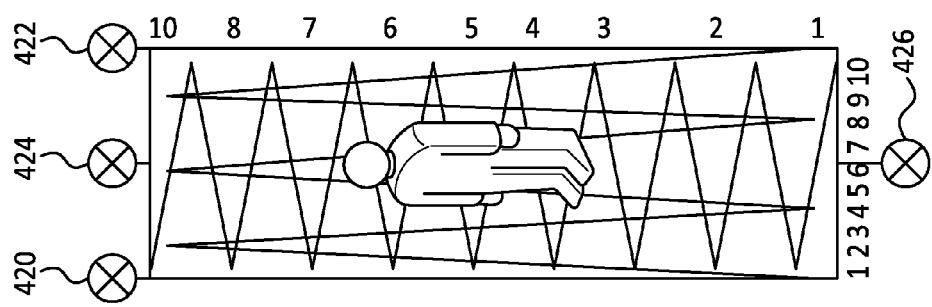

FIGS. 5A-5C are representative of the two bladders 400/402 layered to receive the subject 302. In FIG. 5A, the subject 302 is shown in the center of the bladders 400/402, which would equate to a pressure differential of zero for both bladders 400 and 402. In FIG. 5B, the subject 302 is horizontally centered but not vertically centered. Therefore, the pressure differential of bladder 400 would be zero while the pressure differential of bladder 402 would be C−D, a positive number greater than zero. In FIG. 5C, the subject 302 is neither horizontally centered nor vertically centered. Therefore, the pressure differential of bladder 400 would be A−B, a negative number with an absolute value greater than zero, while the pressure differential of bladder 402 would be C−D, a positive number greater than zero.

Combining and subtracting information from both sets of bladders can also give additional information about the subject's position. In addition to static position, the first derivative of the position information can be used to predict which direction the subject 302 is moving. In addition to the first derivative, the second derivative can be calculated to give the rate at which the subject 302 is moving toward the edge of the bed. This information can be used to predict a bed exit before it actually happens. These predictions using static position or first derivative or second derivative can be used to indicate, such as by an audible alert or a text or email message over the local network or internet, to a care giver that a subject 302 is about to exit a bed. The alert can reduce the number of falls while getting out of bed or help keep track of the subject's 302 movement patterns.

Figure 6:
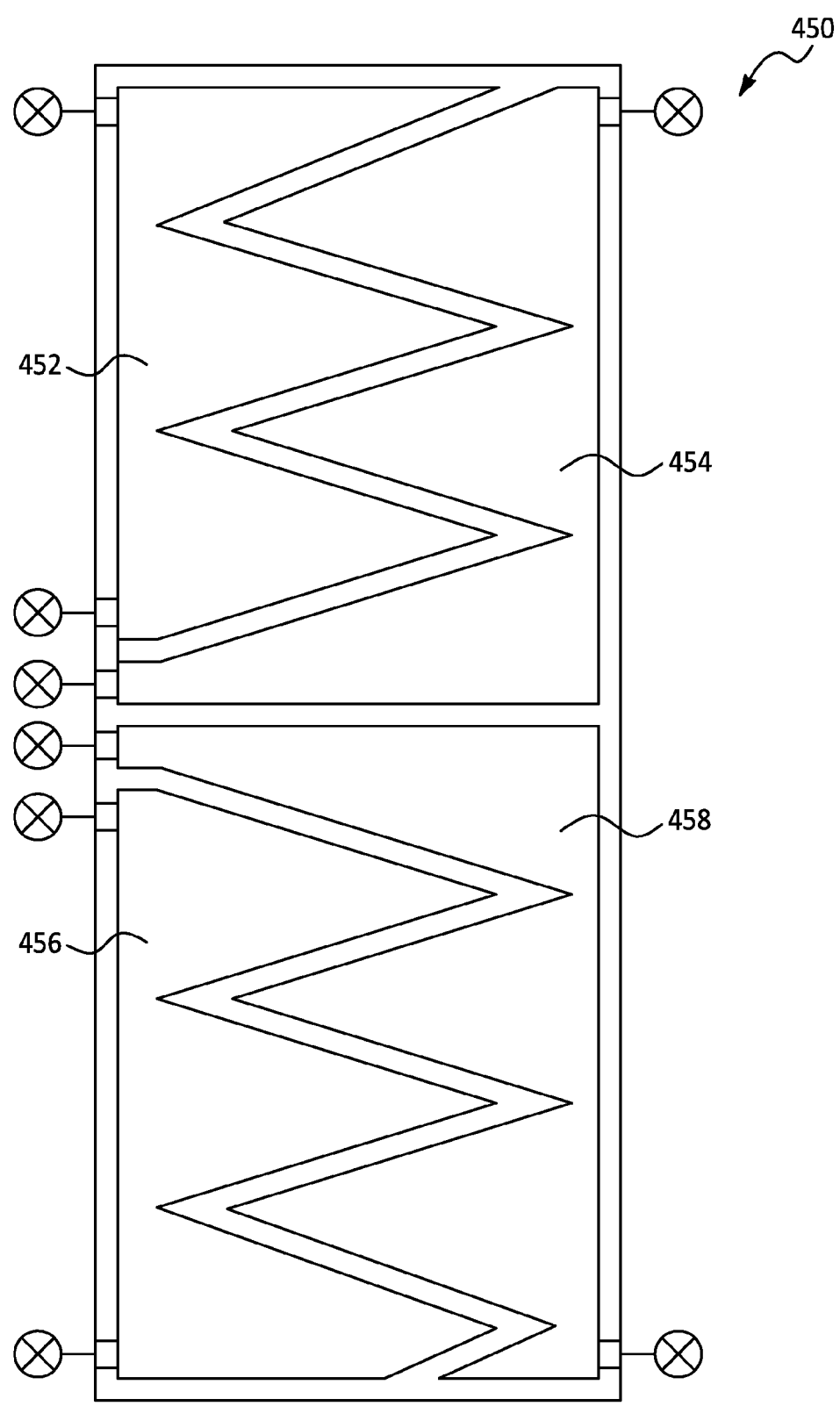
FIG. 6 illustrates another embodiment of a seamed bladder for monitoring a position of a subject using the apparatus of FIG. 3.

FIG. 6 illustrates another embodiment of a seamed bladder 450 for monitoring a position of a subject 302 using the apparatus of FIG. 3. As described above in respect to FIGS. 4A and 4B, the bladder can be divided into more than two portions. As shown in the example embodiment of FIG. 6, the bladder 450 is divided into four portions 452/454/456/458. Each of the four portions 452/454/456/458 has at least two pressure sensors (shown but not numbered). The four portions 452/454/456/458 of FIG. 6 are provided by means of example and are not meant to be limiting. Other numbers of bladder portions, either equal or unequal in portioning, are also contemplated.

Figure 7:
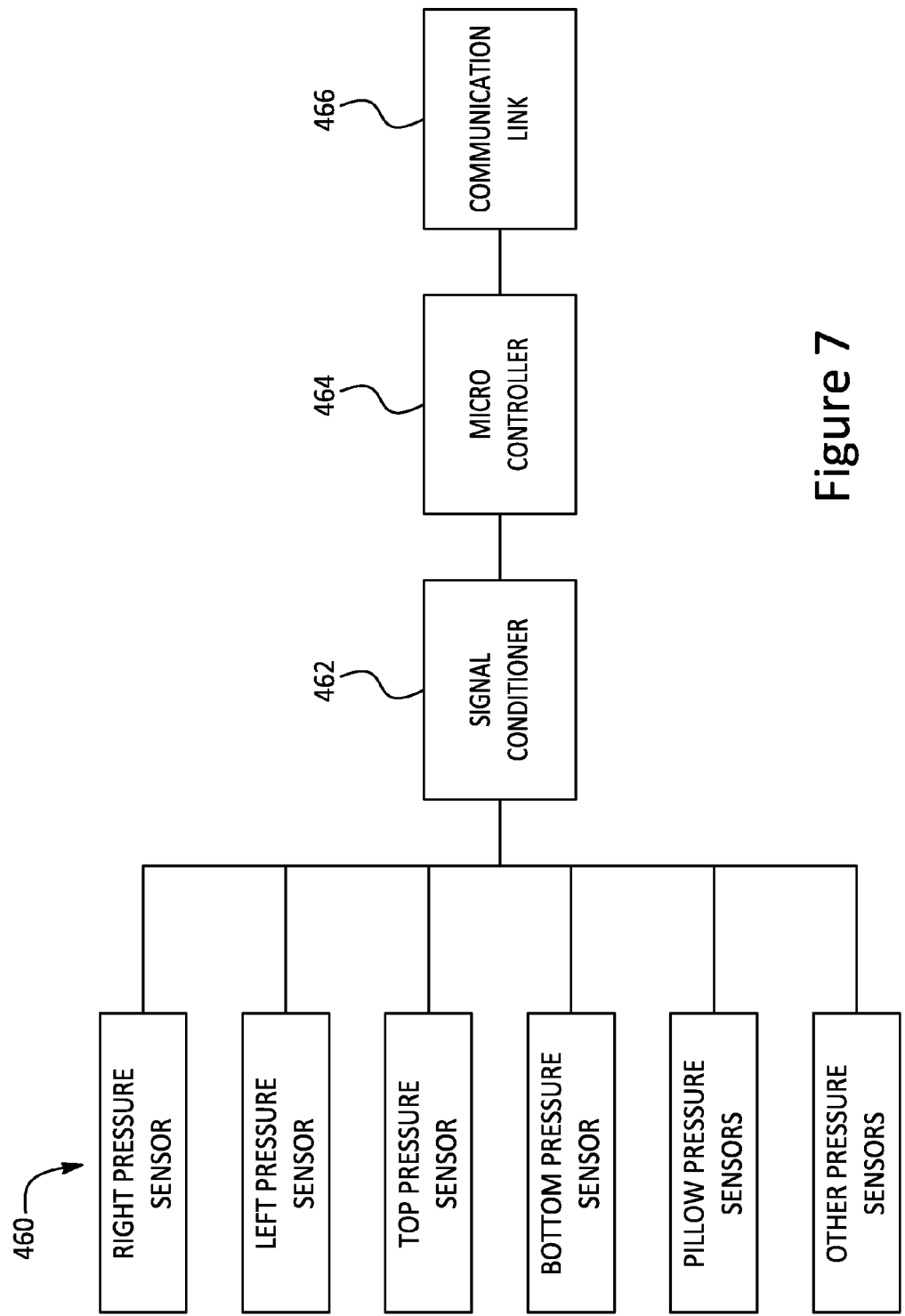
FIG. 7 is a representative system architecture for monitoring the position of a subject in accordance with implementations of this disclosure.

FIG. 7 is representative system architecture for monitoring the position of a subject 302 in accordance with implementations of this disclosure. A group of pressure sensors 460 is shown as including pressure sensors that measure the pressure differential in at least two bladders (right pressure sensor and left pressure sensor for one bladder, top pressure sensor and bottom pressure sensor for another bladder). In addition, pillow pressure sensors and other pressures sensors are also shown in the group of pressure sensors 460 to indicate that additional pressure measurements can be made in association with the system for monitoring the position of the subject 302.

Each sensor in the group of pressure sensors 460 can communicate with a signal conditioner 462. The signal conditioner 462 can analyze the data and/or signals captured by each sensor in the group of pressure sensors 460 by, for example, amplifying, filtering noise, and configuring the data and/or signals for use by a micro controller 464. The micro controller 464 can receive the conditioned pressure signals from the group of pressure sensors 460 and can perform pattern recognition, or other calculations, based on the conditioned pressure signals to determine the position, heart rate, respiratory rate, or other bio-signal properties or conditions associated with the subject 302. The micro controller 464 can send information, such as information indicating the parameters of the subject, such as the position, heart rate, and respiratory rate, to an external device using a communication link 466. The communication link can be any type of wired or wireless communication link such as the communications links 122/124/125/126/128 described in respect to FIG. 1. A method of using the non-intrusive monitoring apparatus 300 equipped with one or more bladders, such as bladders 400/402, is described in respect to FIG. 8 below.

Figure 8:
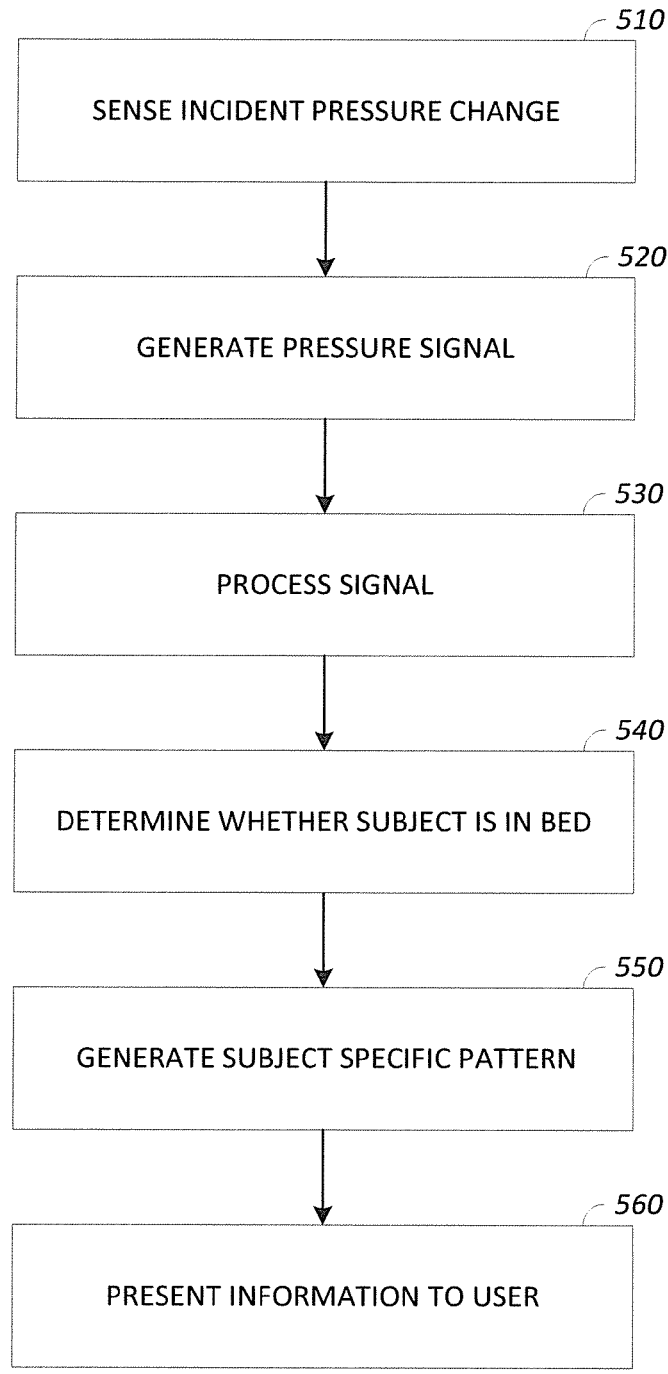
FIG. 8 is a method of monitoring the position of a subject in accordance with implementations of this disclosure.

FIG. 8 shows an example of a method 500 of non-intrusive monitoring using a non-intrusive monitoring apparatus, such as the non-intrusive monitoring apparatus 300 shown in FIG. 3, in accordance with embodiments of this disclosure. For example, non-intrusive monitoring can include monitoring a subject 302 to predict when the subject 302 will exit a bed or mattress or identify when the subject 302 has already vacated the bed or mattress. Non-intrusive monitoring can include sensing an incident pressure change at 510, generating a pressure signal at 520, processing the pressure signal at 530, determining whether the subject 302 is in bed at 540, generating a pattern associated with the subject 302 at 550, presenting information to a user at 560, or any combination thereof.

In some embodiments, an incident pressure change can be sensed at 510. For example, one or more sensors, such as the sensors 420/422/424/426 shown in FIGS. 4 and 5, can receive and measure incident pressure waves within one or more bladders, such as one or both of the divided bladders 400/402 shown in FIGS. 4 and 5. In some embodiments, the one or more sensors 420/422/424/426 can generate signals representing the pressure waves at 520. A different signal can be generated for each of the portions A/B or C/D of the divided bladders 400/402. The sensors 420/422/424/426 can send the generated signals to a control device, such as the monitoring controller 340 shown in FIG. 3.

In some embodiments, the monitoring controller 340 can process the signals at 530. For example, the monitoring controller 340 can store pressure signals or send them to remote storage or can combine pressure signals with other information associated with a subject, such as the subject 302 shown in FIG. 3. The pressure signals, the other information, or both, can be associated with an identifier identifying the subject 302 and with an identifier identifying the substrate, e.g. mattress or bed, associated with the signals.

In some embodiments, the monitoring controller 340 can determine the presence of the subject 302, that is, whether the subject 302 is in bed at 540. For example, the determination can be based on the presence or absence of pressure signals or the magnitude of the pressure signals. For example, a small object, such as a suitcase, would create pressure signals of lower magnitude than a subject 302 lying on the bed. In some embodiments, the control device can determine that a different subject is in the bed. For example, the pressure signals can differ in pattern or magnitude than previously stored pressure signals for the subject 302 associated with, or assigned to, the mattress or bed.

In some embodiments, a pattern associated with the subject 302 can be generated at 550. For example, the pattern can be generated based on the pressure signals and other information associated with the subject 302. The pattern can also be associated with the identifier identifying the subject 302 and with the identifier identifying a bed associated with the subject 302. The pattern can include historical information related to direction of movement of the subject 302, duration of movement of the subject 302, presence of the subject 302, position of the subject 302 over time, or any other indicators or conditions that can be used both to identify a specific subject 302 and predict when the subject 302 is about to exit a mattress or bed.

In some embodiments, information associated with the signal can be presented to a user at 560. For example, information indicating whether the subject 302 is in bed can be sent to an external device for presentation to a user, such as hospital or nursing home personnel. In another example, the information can indicate that a different subject is in the bed. In another example, the information can indicate that the subject 302 is about to exit the bed, based on a pattern for the subject 302 including position of the subject 302 on the bed and direction of movement of the subject 302 that can be associated with previous exits from the bed.

When the subject 302 is a patient, bladders 400/402 can be incorporated into a hospital bed with apparatus 300, and the system can calculate the direction of movement of the patient and can issue an alert when the patient gets to the edge of the bed or has crossed over a predetermined threshold in one or both of the horizontal and vertical positions on the bed. An example threshold 410 is illustrated in FIG. 4A. The threshold 410 can be associated with a predetermined pressure differential, indicating the patient is approaching an edge of the bed. In response to the alert, a caregiver can reach the patient before the patient gets out of bed, reducing the potential for falls, a problem medical facilities work to reduce. Historical position data can be stored and combined with real time position data to assist in earlier and more accurate determinations of a bed exit. Supervision can be provided to the patient when the caregiver receives an indication that a patient is starting to repeat a pattern that was previously associated with an exit from a bed. Being able to provide assistance to patients as they get out of bed can reduce the number of slip and fall accidents in a medical facility setting.

In another example, the subject 302 can be a participant in a rehabilitation or detention program at a public or private facility. Supervisory personnel can be sent to monitor the participant when personnel at the facility receive an indication that the participant is starting to repeat a pattern previously associated with an exit from a substrate, such as a mattress, bed, or chair. Being able to monitor the participant as they attempt to leave a substrate can reduce the number of participants that attempt to get around the rules or regulations of the given program.

The embodiments herein can also be modified to be used in an automobile seat. When used with an automotive seat, the subject 302 can be the driver of a vehicle and the apparatus can create a sleepiness score based on one or more vital signs. The sleepiness score can, for example, indicate impending sleep when heart rate is low, when respiratory rate is low, and when movements are infrequent. Over time, the database can accumulate sleepiness scores for a variety of conditions (e.g., a lower pressure in one or more bladders, a high pressure in one or more bladders, a cool temperature, and/or a warm temperature). An association can then be made using the sleepiness information between the sleepiness score and environmental conditions, such as the pressure in the one or more bladders and the temperature within the vehicle. The association can be performed by the controller or another processor in communication with the database.

The association between the sleepiness score and environmental conditions can include, for example, determining a correlation between the sleepiness score and environmental conditions. Based on the association, a pressure setting can be determined for customizing the environmental conditions (e.g., pressure in the one or more bladders and temperature in the vehicle) to achieve a low sleepiness score. The embodiments herein adapted for use in an automobile seat can capture positional data over time and feed the results to the control unit to send commands to the pump to inflate or deflate the bladders to manipulate the position of the driver against the automobile seat.

The non-intrusive monitoring system can also be used for many applications in a home setting. There is no extensive training, preparation, or change in a subject's behavior in order to incorporate the system into regular use. A medical facility might send such a system home with a patient upon discharge and use an on-site monitoring program to actively monitor that patient's parameters or conditions for a period of time following major surgery, for example. Professional home health care providers can also use the system to enhance their capabilities and improve care. Non-professional care givers can use the monitoring system to gather data for physicians, set reminders for the turning of a patient or providing medication, etc. Periodic updates can be wirelessly sent to a medical professional. Professional home health care workers and non-professional caregivers can utilize the monitoring system for family members with dementia.

While the embodiments have been described in connection with what is presently considered to be the most practical examples, it is to be understood that the disclosure is not to be limited to these examples but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method for monitoring a subject, comprising:
sensing incident pressure waves generated by the subject moving on a divided bladder having a width and a length, the divided bladder comprising a first interleaved portion and a second interleaved portion, wherein the first interleaved portion has a first set of fingers and the second interleaved portion has a second set of fingers, wherein the first set of fingers is interleaved with the second set of fingers, wherein each of the first and second interleaved portions extends nearly the entire width of the divided bladder so as to define a horizontal axis extending laterally along the first and second interleaved portions with at least one first sensor in fluid communication with the first interleaved portion of the bladder and at least one second sensor in fluid communication with the second interleaved portion of the divided bladder, such that the at least one first sensor detects degree of pressure exerted on the first interleaved portion by the subject and the at least one second sensor detects degree of pressure exerted on the second interleaved portion by the subject;

generating signals substantially concurrently from each of the first and second interleaved portions indicative of the incident pressure waves for each of the first and second interleaved portions of the bladder and sending the signals to a processor;

determining a horizontal position of the subject along the horizontal axis of the interleaved portions of the divided bladder as a function of a difference between the signals from each of the first and second interleaved portions; and generating a horizontal position pattern for the subject over a period of time wherein the horizontal position pattern includes a plurality of positions along the horizontal axis and a trajectory of movement between the plurality of horizontal positions over the period of time.

2. The method of claim 1, further comprising:
sending an indication to an external device if the horizontal position of the subject crosses a threshold, the threshold being along the horizontal axis of the interleaved portions and a certain distance from an edge of a bed in which the divided bladder is incorporated.

3. The method of claim 1, further comprising:
predicting an action of the subject while on the divided bladder based on the horizontal position pattern.

4. The method of claim 3, wherein the action is exiting a bed in which the divided bladder is incorporated.

5. The method of claim 3, further comprising:
communicating information related to the action of the subject to an external device; the information configured to trigger assistance with the action or prevention of the action.

6. The method of claim 3, wherein predicting the action comprises generating an estimated position pattern based on the trajectory of movement in the generated position pattern.

7. The method of claim 6, wherein the estimated position pattern is further based on stored historical position patterns of the subject.

8. The method of claim 1, further comprising:
determining a configuration of the subject on the divided bladder based on one or both of a magnitude and a frequency of the signals from each of the interleaved portions, the configuration being one of lying down, partially reclining, and sitting up, wherein the configuration of the subject is determined in addition to the horizontal position of the subject along the horizontal axis of the interleaved portions.

9. The method of claim 8, wherein determining a configuration comprises distinguishing one or both of a heart rate a respiration rate from the signals.

10. The method of claim 1, and further comprising a second divided bladder having a third interleaved portion and a fourth interleaved portion, wherein the third interleaved portion has a third set of fingers and the fourth interleaved portion has a fourth set of fingers, wherein the third set of fingers is interleaved with the fourth set of fingers, wherein each of the third and fourth interleaved portions extends nearly the entire length of the second divided bladder so as to define a second axis extending along the third and fourth interleaved portions in a direction that is substantially perpendicular to the horizontal axis, wherein the divided bladder and the second divided bladder are stacked, and wherein the method further comprises determining the position of the subject along the second axis as a function of a difference between signals from the third and fourth interleaved portions of the second bladder.

11. A non-intrusive monitoring device for monitoring a subject, the device comprising:
a divided bladder having a width and a length, the divided bladder comprising a first interleaved portion and a second interleaved portion, wherein the first interleaved portion has a first set of fingers and the second interleaved portion has a second set of fingers, wherein the first set of fingers is interleaved with the second set of fingers, wherein each of the first and second interleaved portions extends nearly the entire width of the divided bladder so as to define a horizontal axis extending laterally along the first and second interleaved portions;
one or more first sensors in fluid communication with the first interleaved portion of the divided bladder and one or more second sensors in fluid communication with the second interleaved portion of the divided bladder wherein the one or more first and second sensors are configured to substantially concurrently generate signals in response to pressure variations resulting from movement of a subject horizontally along the horizontal axis of the interleaved portions of the divided bladder; and
a processor configured to:
receive signals from the one or more sensors for each of the interleaved portions;
determine a horizontal position of the subject along the horizontal axis of the interleaved portions of the divided bladder as a function of a difference between the signals from each of the interleaved portions; and
generate a horizontal position pattern for the subject over a period of time wherein the horizontal position pattern includes a plurality of positions along the horizontal axis and a trajectory of movement between the plurality of horizontal positions over the period of time.

12. The device of claim 11, wherein the processor is further configured to:
send an indication to an external device if the position of the subject crosses a threshold, the threshold being along the horizontal axis of the interleaved portions and a certain distance from an edge of a bed in which the divided bladder is incorporated.

13. The device of claim 11, wherein the processor is further configured to:
predict an action of the subject while on the divided bladder based on the position pattern along the horizontal axis.

14. The device of claim 13, wherein the action is exiting a bed in which the divided bladder is incorporated.

15. The device of claim 13, wherein the processor is further configured to:
communicate information related to the action of the subject to an external device; the information configured to trigger assistance with the action or prevention of the action.

16. The device of claim 13, wherein, when predicting the action, the processor is further configured to generate an estimated position pattern based on the trajectory of movement in the generated position pattern.

17. The device of claim 16, wherein the estimated position pattern is further based on stored historical position patterns of the subject.

18. The device of claim 11, wherein the processor is further configured to:
   determine a configuration of the subject on the divided bladder based on one or both of a magnitude and a frequency of the signals from each of the interleaved portions, the configuration being one of lying down, partially reclining, and sitting up, wherein the configuration of the subject is determined in addition to the horizontal position of the subject along the horizontal axis of the interleaved portions.

19. The device of claim 11, and further comprising a second divided bladder having a third interleaved portion and a fourth interleaved portion, wherein the third interleaved portion has a third set of fingers and the fourth interleaved portion has a fourth set of fingers, wherein the third set of fingers is interleaved with the fourth set of fingers, wherein each of the third and fourth interleaved portions extends nearly the entire length of the second divided bladder so as to define a second axis extending along the third and fourth interleaved portions in a direction that is substantially perpendicular to the horizontal axis, wherein the divided bladder and the second divided bladder are stacked, and wherein the processor determines position of the subject along the second axis as a function of a difference between signals from the third and fourth interleaved portions.

20. The device of claim 11, wherein at least some fingers in the first set of fingers are substantially triangular so as to taper substantially continuously in a direction extending along the horizontal axis from the first interleaved portion toward the second interleaved portion and wherein at least some fingers in the second set of fingers are substantially triangular so as to taper substantially continuously in a direction extending along the horizontal axis from the second interleaved portion toward the first interleaved portion.

21. The device of claim 11, wherein the first and second sets of fingers are configured such that pressure changes substantially linearly in each of the first and second interleaved portions of the divided bladder as the subject moves horizontally along the horizontal axis of the interleaved portions such that the horizontal position of subject along the horizontal axis can be determined in a linear manner as the function of the difference between the signals from each of the interleaved portions.

22. The device of claim 11, wherein the divided bladder comprises a seam separating the divided bladder into the first and second interleaved portions.

23. The device of claim 11, wherein the divided bladder comprises a seam extending substantially in a zig-zag pattern and separating the divided bladder into the first and second interleaved portions.

24. A device for monitoring the position of a subject on a substrate, comprising:
   a sensing unit having a divided bladder having a width and a length, the divided bladder comprising a first interleaved portion and a second interleaved portion, wherein the first interleaved portion has a first set of fingers and the second interleaved portion has a second set of fingers, wherein the first set of fingers is interleaved with the second set of fingers, wherein each of the first and second interleaved portions extends nearly the entire width of the divided bladder so as to define a horizontal axis extending laterally along the first and second interleaved portions, and one or more sensors in fluid communication with each of the first and second interleaved portions, wherein the one or more sensors are configured to sense pressure variations within the divided bladder generated by movement of the subject along the horizontal axis of the interleaved portions and to generate signals indicative of the pressure variations;
   a processor configured to receive the signals and to determine and generate output indicative of a time-based pattern of the subject's horizontal position along the horizontal axis on the substrate as a function of the difference between the signals from each of the first and second interleaved portions; and
   an external device configured to display the output.

* * * * *

UNITED STATES PATENT AND TRADEMARK OFFICE
CERTIFICATE OF CORRECTION

PATENT NO. : 9,445,751 B2
APPLICATION NO. : 13/945554
DATED : September 20, 2016
INVENTOR(S) : Steven Jay Young, Carl Hewitt and Al Luckow It is certified that error appears in the above-identified patent and that said Letters Patent is hereby corrected as shown below:

In the Claims

Column 17, Line 55: In Claim 9, after "rate" second occurrence insert -- and --.

Signed and Sealed this
Twenty-first Day of February, 2017

Michelle K. Lee
*Director of the United States Patent and Trademark Office*